United States Patent [19]

Cowart et al.

[11] Patent Number: 5,362,747
[45] Date of Patent: Nov. 8, 1994

[54] 2-NITROARYL AND 2-CYANOARYL COMPOUNDS AS REGULATORS OF NITRIC OXIDE SYNTHASE

[75] Inventors: Marlon Cowart, Round Lake Beach; James F. Kerwin, Grayslake, both of Ill.

[73] Assignee: Abbott Laboratories, Abbott Park, Ill.

[21] Appl. No.: 147,241

[22] Filed: Nov. 3, 1993

Related U.S. Application Data

[63] Continuation-in-part of Ser. No. 981,585, Nov. 25, 1992, abandoned.

[51] Int. Cl.$^5$ ............... A61K 31/135; A61K 31/195; A61K 31/24; C07C 215/68
[52] U.S. Cl. .................... 514/448; 514/471; 514/510; 514/520; 514/522; 514/524; 514/538; 514/562; 514/563; 514/564; 514/617; 514/649; 514/653; 549/72; 549/487; 558/414; 558/417; 558/422; 560/10; 560/17; 560/21; 560/22; 562/427; 562/431; 562/435; 562/437

[58] Field of Search .............. 549/72, 487; 558/414, 558/417, 422; 560/10, 17, 21, 22; 562/427, 431, 435, 437; 564/182, 185, 219, 220, 341, 355, 367; 514/448, 471, 510, 520, 522, 524, 538, 562, 563, 564, 617, 649, 653

[56] References Cited

PUBLICATIONS

Kooistra et al, Biochemistry, vol. 17(1978) pp. 345–351.
Gagnon et al, Can. J. Chem., vol. 30(1952) pp. 592–597.

*Primary Examiner*—Richard L. Raymond
*Attorney, Agent, or Firm*—Richard A. Elder; Edward H. Gorman, Jr.; James D. McNeil

[57] ABSTRACT

2-Nitroaryl or 2-cyanoaryl compounds of the formula

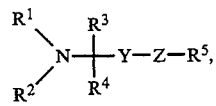

pharmaceutical compositions thereof, intermediates useful in the preparation of these compounds, and methods for treating disorders of vascular smooth muscles or diseases of the cartilage, macrophages, neurons, platelets, bronchial smooth muscles, optic muscles and gastrointestinal smooth muscles, in addition to sickle cell anemia, diabetes, synovitis, chondroarthritis and osteoarthritis by employing these compounds.

8 Claims, No Drawings

2-NITROARYL AND 2-CYANOARYL COMPOUNDS AS REGULATORS OF NITRIC OXIDE SYNTHASE

CROSS REFERENCE TO OTHER RELATED APPLICATIONS

This application is a continuation-in-part of copending U.S. patent application Ser. No. 07/981,585, filed Nov. 25, 1992, now abandoned.

TECHNICAL FIELD

The present invention relates to novel 2-nitroaryl and 2-cyanoaryl compounds, to compositions thereof useful in regulating the production of soluble guanylate cyclase or nitric oxide, to intermediates useful in the production thereof, and to a method of treating disorders of the vascular system or diseases of the cartilage, including hypotension, hypertension, coronary vasospasm, cerebral vasoconstriction, cardiomyopathy, atherogenesis, atherosclerosis, myocardial ischemia, cerebral ischemia, diabetes, endotoxemia, sepsis, asthma and rhinitis, synovitis, chondroarthritis and osteoarthritis.

BACKGROUND OF THE INVENTION

Furchgott (*Nature*, 1980, 288:373–6) reported in 1980 that endothelial cells release a powerful vasodilator which is termed endothelium-derived relaxing factor (EDRF). Subsequent research has shown that many endothelium-dependent receptor agonists, including, for example, adenosine diphosphate (ADP), adenosine triphosphate (ATP), 5-hydroxytryptamine (5-HT), thrombin, acetylcholine (ACh), vasoactive intestinal polypeptide (VIP), oxytocin, cholecystokinin (CCK), calcitonin gene-related peptide, noradrenaline, histamine, calcium ionophores, melittin and ergometrine invoke the release of EDRF. The release of EDRF, in turn, stimulates the soluble form of the enzyme guanylate cyclase, thereby increasing levels of the second messenger, cyclic guanosine monophosphate (cGMP), which, in turn, produces vasorelaxation. Reviews are available which discuss this process in more detail (see, for example, A. M. Katz, *J. Am. Coll. Cardiol.*, 1988, 12: 797–806; J. A. Angus and T. M. Cocks, *Pharmaceutical Therapeutics*, 1989, 41: 303–52; S. A. Waldman and F. Murad, *Pharmacological Reviews*, 1987, 39: 163–196; F. Murad, *J. Clin. Invest.*, 1986, 78: 1–5; L. J. Ignarro, *Biochem. Pharmacol.*, 1991, 41: 485–90; and S. Moncada, R. M. J. Palmer and E. A. Higgs, *Pharmacological Reviews*, 1991, 43: 109–142).

Pharmacological characterization of EDRF and its effects has been an active area of research over the past eleven years (K. Shikano et al., *J. Pharmacol. Exp. Therap.*, 1988, 247:873–81 and L. J. Ignarro, *Annu. Rev. Pharmacol. Toxicol.*, 1990, 30: 535–60), and now there is substantial evidence that nitric oxide (NO) is the major endothelium-derived relaxing factor (R. M. J. Palmer et al., Nature, 1987, 327: 524–6; S. Moncada et al, *Biochem. Pharmacol.*, 1989, 38: 1709–15; and S. Moncada et al., *Hypertension*, 1989, 12: 365–72). In particular, nitric oxide (NO) was tested and found to elicit a potent and transient relaxation of bovine coronary artery accompanied by cGMP accumulation (C. A. Guetter et al., *J. Cyclic Nucleotide Res.*, 1979, 5:211–24) and it was also shown to activate soluble guanylate cyclase and to elevate tissue cGMP levels.

Recent reports (H. H. H. W. Schmidt et al., *European J. Pharmacol.*, 1988, 154:213–6 and S. Moncada et al., *Hypertension*, 1988, 12: 365–72) have suggested that L-arginine may be the endogenous source of EDRF (NO), and this hypothesis is further supported by the observation that EDRF (NO) production is inhibited by the simple arginine derivative, $N^G$-methylarginine (R. M. J. Palmer et al., *Biochem. Biophys. Res. Comm.*, 1988, 153: 1251–56; S. Moncada et al., *Biochemical Pharmacology*, 1988, 37: 2495–2501; and I. Sakuma et al., *Proc. Nat. Acad. Sci. USA*, 1988, 85: 8664–7).

Increasing evidence has been uncovered that suggests EDRF or EDRF-like substances may also control cGMP production in non-endothelial cells (J. Garthwaite, *Nature*, 1988, 336:385–388 and T. J. Rimele et al., *J. Pharmacol. Exp. Therap.*, 1988, 245:102–111) and that this method of guanylate cyclase regulation may be ubiquitous. A role in the regulation of neural transmission and a role in the neural control of gastrointestinal smooth muscle function has been elucidated (J. Collier and P. Vallance, *Trends in Pharmacological Sciences*, 1989, 428–31 and K. M. Desai et al., *Nature*, 1991, 351: 477–9). Compounds that control, inhibit, or otherwise regulate this pathway, therefore, have potentially many and varied therapeutic applications, for instance, as analgesics (Duarte et al., *European J. Pharmacology*, 1990, 186: 289–93), as cerebroprotectives (cf. Southham et al., *J. Neurochem.*, 1991, 56: 2072–81) and as hypocholesteremics (Cooke et al., *Circulation*, 1991, 83: 1057–62).

Recent work has shown that there are many isoforms of the EDRF (NO) synthase enzyme. The primary distinction between these isoforms is whether they are constitutive or inducible forms, but other factors which serve to distinguish these isoforms are their cellular localization and their cofactor requirements. Many of these isoforms have been arbitrarily given Roman numeral designations and are described in the table below, wherein NADPH represents reduced nicotinamide adenine dinucleotide phosphate, $BH_4$ represents tetrahydrobiopterin, FAD represents flavin adenine dinucleotide and FMN represents flavin mononucleotide.

| Type | Cosubstrates % Cofactors | Regulated by | $M_r$ of denatured protein* | Present in |
|---|---|---|---|---|
| I (soluble) | NADPH, $BH_4$ | $Ca^{++}$, calmodulin | 155 kDa** | brain and cerebellum |
| II (soluble) | NADPH, $BH_4$, FAD/FMN, thiols, $Mg^{++}$ | induced by endotoxin and cytokines | 125–135 kKa** | macrophages |
| III (particulate) | NADPH $BH_4$ | $Ca^{++}$, calmodulin | 135 kDa** | endothelial cells |

*Molecular weight determination by sodium dodecyl sulfate/polyacrylamide gel elecrophoresis
**kilo Daltons Isoform I has been purified and characterized by Bredt and Snyder (*Proc. Natl. Acad. Sci. USA*, 1989, 87: 682–685) and by Schmidt et al. (*Proc. Natl. Acad. Sci.*

USA, 1989, 88: 365–369). Isoform II has been purified and characterized by Kawai et al. (J. Biological Chemistry, 1991, 266: 12544–47). Isoform III has been purified and characterized by Pollock et al. (Proc. Natl. Acad. Sci. USA, 1991, 88: 10480–4). Isoform-specific agents may offer the advantage of selectivity, i.e., desired therapeutic effect with fewer or more tolerable side-effects.

Compounds which act directly to regulate NO synthesis or in an indirect fashion to regulate the production of cGMP through regulation of the effect of endogenous EDRF (NO) on soluble guanylate cyclase are useful in the treatment of those disease states associated with smooth muscle and smooth muscle tone, especially those involving airway, gastrointestinal and vascular muscle, and platelet function. Examples of such conditions include hypotension, endotoxemia, shock, sepsis, rhinitis, hypertension, and cerebral vasoconstriction and vasodilation, such as migraine and non-migraine headache, ischemia, thrombosis, and platelet aggregation, including preservation and processing of platelets for transfusions and perfusion technologies. Additional examples include atherosclerosis, diseases of the bronchial passages, such as asthma, diseases of the optic musculature, diseases of the gastrointestinal system, such as reflux esophagitis (GERD), spasm, diarrhea, irritable bowel syndrome, and other gastrointestinal motile dysfunctions. Such compounds may also find use in angioplasty and the treatment of sickle cell anemia.

Examples of known compounds that act to regulate the production of cGMP by this method may be grouped into four categories: (1) those compounds, for example, methylene blue, which directly or indirectly (through superoxide anion) oxidize EDRF (NO) and thereby inactivate it (R. J. Gryglewski et al., Nature, 1988, 320:454–6 and S. Moncada et al., Proc. Natl. Acad. Sci. USA, 1986, 83: 9164–68); (2) those agents, for example, hemoglobin, which directly bind either EDRF (NO) itself or one of its end products; (3) those agents which remove superoxide anion $(O_2)^-$ and other oxidants, thereby enhancing the effect of EDRF (for example, the enzyme superoxide dismutase removes superoxide anion by converting it to molecular oxygen ($O_2$) and hydrogen peroxide); and (4) the nitrovasodilators, such as nitroglycerin, which provide nitrogen oxide to stimulate guanylate cyclase (F. Murad, J. Clin. Invest., 1986, 78: 1–5). With the exception of the nitrovasodilators, none of these categories of compounds has provided a viable therapeutic agent for the regulation of cGMP production in disease states. The nitrovasodilators, because they provide nitrogenous oxides indiscriminately to numerous target tissues, and thus lead to such complications as tolerance (A. Mulsch et al., European J. Pharmacol., 1988, 158: 191–8), may not be the ultimate therapeutic agents of choice. More recently it has been reported that N-hydroxyarginine is a substrate for the NO synthase enzyme (Steuhr et al., J. Biol. Chem., 1991, 266: 6259).

SUMMARY OF THE INVENTION

The present invention is directed to regulators of soluble guanylate cyclase or nitric oxide production which have the formula:

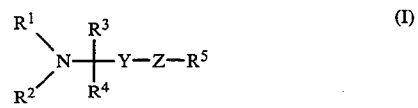

or a pharmaceutically-acceptable salt, ester, amide or prodrug thereof.

It is also directed to pharmaceutical compositions comprising a therapeutically-effective amount of a compound of formula (I) and a pharmaceutically-acceptable carrier or diluent, to intermediates useful in the preparation of compounds of formula (I); and to a method of treating disorders of vascular smooth muscles or diseases of the cartilage, macrophages, neurons, platelets, bronchial smooth muscles, optic muscles and gastrointestinal smooth muscles, in addition to treating sickle cell anemia, diabetes, synovitis, chondroarthritis and osteoarthritis, by administration of a compound of formula (I) to humans and mammals in need of such treatment.

DETAILED DESCRIPTION OF THE INVENTION

This invention relates to novel 2-nitroaryl and 2-cyanoaryl compounds and pharmaceutical compositions thereof which regulate soluble guanylate cyclase by either inhibiting or promoting the synthesis of its primary regulator factor, EDRF (nitric oxide), e.g., by inhibiting or promoting the action of nitric oxide directly or indirectly. These compounds may, therefore, be used in the treatment of disorders of vascular smooth musculature, macrophages, neurons, and platelets, including: hypotension, endotoxemia, sepsis, hypertension, shock, cerebral vasoconstriction, cerebral vasodilation, headache, disease states involving platelet aggregation, including preparation of platelets for transfusion, use in angioplasty, ischemia, thrombosis, coronary vasospasm, cardiomyopathy, atherogenesis, atherosclerosis, sickle cell anemia and diabetes, diseases involving the bronchial passages such as asthma, diseases of the optic musculature, and diseases of the gastrointestinal system, such as diarrhea, irritable bowel syndrome, spasm, and esophagitis (GERD), and diseases of the cartilage, such as synovitis, chondroarthritis and osteoarthritis. The invention also relates to intermediates useful in the preparation of these novel 2-nitroaryl and 2-cyanoaryl compounds.

In particular, the invention relates to compounds of formula (I):

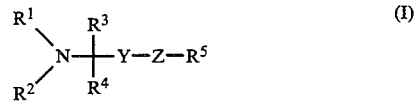

or a pharmaceutically-acceptable salt, ester, amide or prodrug thereof, wherein
$R^1$ is selected from the group consisting of
(1) hydrogen;
(2) $C_1$–$C_6$-alkyl;
(3) $C_6$–$C_{12}$-aryl-$C_1$–$C_4$-alkyl, as defined below;
(4) substituted $C_6$–$C_{12}$-aryl-$C_1$–$C_4$-alkyl, as defined below;
(5) N-protecting group, as defined below;
(6) —CO—$C_1$–$C_6$-alkyl, wherein CO is carbonyl;

(7) —CO—$C_6$-$C_{12}$-aryl, wherein $C_6$-$C_{12}$-aryl is as defined below;

(8) —CO-substituted $C_6$-$C_{12}$-aryl, wherein substituted $C_6$-$C_{12}$-aryl as defined below;

(9) —CO—($C_6$-$C_{12}$-aryl-$C_1$-$C_4$-alkyl);

(10) —CO-(substituted $C_6$-$C_{12}$-aryl-$C_1$-$C_4$-alkyl); and

(11) —CO—Het, wherein Het is as defined below;

$R^2$ is hydrogen when $R^1$ is selected from options (5)-(11) above, or when $R^1$ is selected from options (1)-(4) above, additionally $C_1$-$C_6$-alkyl, $C_6$-$C_{12}$-aryl-$C_1$-$C_4$-alkyl, or substituted $C_6$-$C_{12}$-aryl-$C_1$-$C_4$-alkyl;

$R^3$ is selected from the group consisting of:

(1) —CO—$OR^6$, wherein $R^6$ is hydrogen, $C_1$-$C_6$-alkyl, $C_2$-$C_6$-alkenyl, cyclo-$C_3$-$C_7$-alkyl, $C_6$-$C_{12}$-aryl, substituted $C_6$-$C_{12}$-aryl, $C_6$-$C_{12}$-aryl-$C_1$-$C_4$-alkyl, or substituted $C_6$-$C_{12}$-aryl-$C_1$-$C_4$-alkyl;

(2) —$CHR^7$—$OR^8$, wherein $R^7$ is hydrogen, $C_1$-$C_6$-alkyl, cyclo-$C_3$-$C_7$-alkyl, $C_2$—$C_4$-alkenyl, or $C_6$-$C_{12}$-aryl and $R^8$ is hydrogen, $C_1$-$C_6$-alkyl, or an oxygen protecting group, as defined below; and (3)

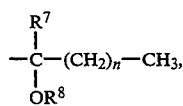

wherein n is 0-2, and $R^7$ and $R^8$ are as defined above;

$R^4$ is hydrogen, $C_1$-$C_6$-alkyl, $C_6$-$C_{12}$-aryl-$C_1$-$C_3$-alkyl or substituted $C_6$-$C_{12}$-aryl-$C_1$-$C_3$-alkyl;

Y is

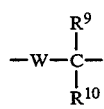

wherein W is selected from
(a) $C_2$-$C_4$-alkylene;
(b) $C_2$-$C_4$-alkenylene;
(c) $C_2$-$C_4$-alkynylene;
(d) 1,4-(cyclo-$C_5$-$C_7$-alkylene), as defined below;
(e) 1,4-(cyclo-$C_5$-$C_7$-alkenylene), as defined below;
(f) phenylene, as defined below;
(g) $C_1$-$C_3$-alkylene-phenylene, as defined below; and
(h) phenylene-$C_1$-$C_3$-alkylene, as defined below; and $R^9$ and $R^{10}$ are independently hydrogen or $C_1$-$C_6$-alkyl;

Z is S or $NR^{11}$, wherein $R^{11}$ is hydrogen, $C_1$-$C_6$-alkyl, $C_6$-$C_{12}$-aryl-$C_1$-$C_4$-alkyl or substituted $C_6$-$C_{12}$-aryl-$C_1$-$C_4$-alkyl; and $R^5$ is

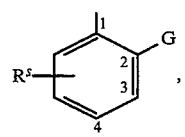

wherein G is either nitro or cyano; and $R^S$ represents one or two substituents substituted at the 3-, 5- or 6-positions, where these substituents are independently selected from the group consisting of:
(a) halogen;
(b) $C_1$-$C_4$-alkyl;
(c) $C_1$-$C_4$-alkoxy;
(d) $C_1$-$C_4$-thioalkoxy;
(e) hydroxy;
(f) carbo-$C_1$-$C_4$-alkoxy;
(g) cyano; and
(h) halo-$C_1$-$C_4$-alkyl; or

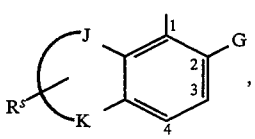

wherein G and $R^S$ are as defined above, and J and K taken together with the existing ring represent a fused bi- or tricyclic carbocycle of from 9–14 carbon atoms, as defined below, wherein $R^S$ may be substituted anywhere within the entire bi- or tricyclic ring system except the 4-position.

In one embodiment of the present invention are compounds of Formula I above, wherein $R^1$ is hydrogen or an N-protecting group, $R^2$ is hydrogen, $R^3$ is $COOR^6$, wherein $R^6$ is as defined above, $R^4$ is hydrogen, $R^5$ is

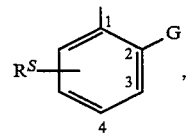

wherein G and $R^S$ are as defined above and Y and Z are as defined above.

In another embodiment of the present invention are compounds of Formula I above, wherein $R^1$ is hydrogen or an N-protecting group, $R^2$ is hydrogen, $R^3$ is $CHR^7OR^8$, wherein $R^8$ is as defined above and $R^7$ is hydrogen, $R^4$ is hydrogen, $R^5$ is

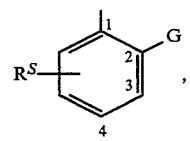

wherein G and $R^S$ are as defined above, and Y and Z are as defined above.

In a preferred embodiment of the present invention are compounds of Formula I above, wherein $R^1$ is hydrogen or an N-protecting group, $R^2$ is hydrogen, $R^4$ is hydrogen, $R^5$ is

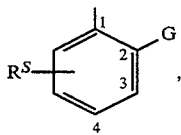

wherein G is NO₂ and $R^S$ is a single substituent at the 5-position, and $R^3$, Y and Z are as defined above.

Representative compounds according to the present invention include:

(2S)-2-Amino-5-(5-methyl-2-nitrophenylamino)pentanoic acid;
(2S)-2-Amino-5-(5-methyl-2-nitrophenylamino)-pent-3E-en-1-ol;
2-Amino-5-(5-methyl-2-nitrophenylamino )-1-pentanol;
(2S)-2-Amino-5-(5-hydroxy-2-nitrophenylamino)pentanoic acid;
(2S)-2-Amino-5-(5-methoxy-2-nitrophenylamino)pentanoic acid;
(2S)-2-Amino-5-(2-chloro-6-nitrophenylamino)pentanoic acid;
(2S)-2-Amino-6-(2-nitro-5-methylphenylamino)hexanoic acid;
(2S)-2-Amino-5-(5-methyl-2-nitrophenylthioxy)pentanoic acid;
(2R)-2-(N-(1,1 -Dimethylethoxycarbonyl)amino)-5-(5-methyl-2-nitrophenylamino)pentanoic acid;
(2R)-2-Amino-5-(5-methyl-2-nitrophenylamino)pentanoic acid;
2-Amino-4-(5-methyl-2-nitrophenylamino)butanoic acid;
(2S)-2-Amino-6-(2-nitrophenyamino)hexanoic acid;
(2S)-2-(Benzyloxycarbonylamino)-5-(5-methyl-2-nitrophenoxy)pentanoic acid t-butyl ester;
(2S)-3-[2-(2-Nitro-5-methylphenylamino)ethylthioxy]propanoic acid;
$N^2$-Boc-2-amino-5-(5-methyl-2-nitrophenylamino)-1-phenyl-1-pentanol;
$N^3$-Boc-3-amino-6-(5-methyl-2-nitrophenylamino)-2-phenyl-2-hexanol;
2(S)-Amino-5-(5-methyl-2-nitrophenylthioxy)pentanol;
$N^2$-Hexanoyl-(2S)-2-amino-5-(5-methyl-2-nitrophenylamino)pentanoic acid;
$N^2$-Hexanoyl-(2S)-2-amino-5-(5-methyl-2-nitrophenylthioxy)pentanoic acid;
2-Amino-5-(5-methyl-2-nitrophenylamino)-1-phenyl-1-pentanol;
3-Amino-6-(5-methyl-2-nitrophenylamino)-2-phenyl-2-hexanol;
4-(5-Methyl-2-nitrophenylamino)phenyl-(S)-glycine;
$N^2$-Benzoyl-2(S)-amino-5-(5-methyl-2-nitrophenylamino)pentanoic acid;
$N^2$-Acetyl-2(S)-amino-5-(5-methyl-2-nitrophenylamino)pentanoic acid;
$N^2$-Phenylacetyl-2(S)-amino-5-(5-methyl-2-nitrophenylamino)pentanoic acid;
$N^2$-Trifluomacetyl-2(S)-amino-5-(5-methyl-2-nitrophenylamino)pentanoic acid;
$N^2$-(4-Phenyl-2E-butenoyl)-2 ( S )-amino-5-(5-methyl-2-nitrophenylamino)pentanoic acid;
$N^2$-(2E-Butenoyl)-2(S)-amino-5-(5-methyl-2-nitrophenylamino)pentanoic acid;
$N^2$-(2-Methylpropanoyl )-2(S)-amino-5-(5-methyl-2-nitrophenylamino)pentanoic acid;
$N^2$-(2-Furoyl)-2(S)-amino-5-(5-methyl-2-nitrophenylamino)pentanoic acid;
$N^2$-(Cyclohexanecarbonyl)-2(S)-amino-5-(5-methyl-2-nitrophenylamino)pentanoic acid;
$N^2$-(Thiopheneacetyl)-2(S)-amino-5-(5-methyl-2-nitrophenylamino)pentanoic acid;
$N^2$-(Cyclopropanecarbonyl)-2(S)-amino-5-(5-(methyl-2-nitrophenylamino)pentanoic acid;
$N^2$-Benzoyl-2(S)-amino-5-(5-methyl-2-nitrophenylthioxy)pentanoic acid;
$N^2$-Acetyl-2(S)-amino-5-(5-methyl-2-nitrophenylthioxy)pentanoic acid;
$N^2$-Phenylacetyl-2(S)-amino-5-(5-methyl-2-nitrophenylthioxy)pentanoic acid;
$N^2$-Trifluoroacetyl-2(S)-amino-5-(5-methyl-2-nitrophenylthioxy)pentanoic acid;
$N^2$-(4-Phenyl-2E-butenoyl)-2(S)-2-amino-5-(5-methyl-2-nitrophenylthioxy)pentanoic acid;
$N^2$-(2E-Butenoyl)-2(S)-amino-5-(5-methyl-2-nitrophenylthioxy)pentanoic acid;
$N^2$-(2-Methylpropanoyl)-2(S)-amino-5-(5-methyl-2-nitrophenylthioxy)pentanoic acid;
$N^2$-(2-Furoyl)-2(S)-amino-5-(5-methyl-2-nitrophenylthioxy)pentanoic acid;
$N^2$-(Cyclohexanecarbonyl)-2(S)-amino-5-(5-methyl-2-nitrophenylthioxy)pentanoic acid;
$N^2$-(Thiopheneacetyl)-2(S)-amino-5-(5-methyl-2-nitrophenylthioxy)pentanoic acid;
$N^2$-(Cyclopropanecarbonyl)-2(S)-amino-5-(5-methyl-2-nitrophenylthioxy)pentanoic acid;
3-Amino-6-(5-methyl-2-nitrophenylamino)-2-hexanol;
4-Amino-7-(5-methyl-2-nitrophenylamino)-1-hepten-3-ol;
4-Amino-7-(5-methyl-2-nitrophenylamino)-3-heptanol;
5-Amino-8-(5-methyl-2-nitrophenylamino)-2-methyl-4-octanol;
5-Amino-8-(5-methyl-2-nitrophenylamino)-1-octen-4-ol;
6-Amino-9-(5-methyl-2-nitrophenylamino)-5-nonanol;
2-Amino-5-(5-methyl-2-nitrophenylamino)-1-phenyl-1-pentanol;
2-Amino-5-(5-methyl-2-nitrophenylamino)-1-(2'-thienyl)-1-pentanol;
2-Amino-5-(5-methyl-2-nitrophenylamino)-1-(cyclopentyl)-1-pentanol;
2-Amino-5-(5-methyl-2-nitrophenylamino)-1-(cyclohexyl)-1-pentanol;
3-Amino-6-(5-methyl-2-nitrophenylamino)-2-hexanone;
(2S)-Amino-5-(2-nitro-5-bromonaphthylamino)-pent-3E-enol;
(2S)-Amino-5-(6-nitro-2,3-dimethyl-phenylamino)-pent-3E-enol;
(2S)-Amino-5-(2-nitro-5-chloro-phenylamino)-pent-3E-enol;
(2S)-Amino-5-(2-nitro-6-methyl-phenylamino)-pent-3E-enol;
(2S)-Amino-5-(2-nitro-3-methyl-phenylamino)-pent-3E-enol;
(2S)-Amino-5-(2-nitro-5-fluoro-phenylamino)-pent-3E-enol;
(2S)-Amino-5-(2-nitro-6-chloro-phenylamino)-pent-3E-enol;
(2S)-Amino-5-(2-nitro-5-chloro-phenylamino)-pent-3E-enol;
(2S)-Amino-5-(6-nitro-2,3-dichloro-phenylamino)-pent-3E-enol;
(2S)-Amino-5-(2-nitro-5-hydroxy-phenylamino)-pent-3E-enol;
(2S)-Amino-5-(2-nitro-5-chloro-6-methylphenylamino)-pent-3E-enol;

(2S)-Amino-5-(2-nitro-5-fluoro-phenylamino)-pent-3E-enol;

(2S)-Amino-5-(2-nitro-6-chloro-phenylamino)-pent-3E-enol;

(2S)-Amino-5-(2-nitro-5-chloro-phenylamino)-pent-3E-enol;

(2S)-Amino-5-(6-nitro-2,3-dichloro-phenylamino)-pent-3E-enol;

(2S)-Amino-5-(2-nitro-5-hydroxy-phenylamino)-pent-3E-enol;

(2S)-Amino-5-(2-nitro-5-chloro-6-methylphenylamino)-pent-3E-enol;

(2S)-Amino-5-(2-nitro-5-bromo-naphthylamino)pentanoic acid; and (2S)-Amino-5-(2-nitro-5-cyano-naphthylamino)pentanoic acid.

Representative of the preferred compounds of the invention are:

(2S)-2-Amino-5-(5-methyl-2-nitrophenylamino)pentanoic acid;

2-Amino-5-(5-methyl-2-nitrophenylamino)-pent-3E-en-1ol;

2-Amino-5-(5-methyl-2-nitrophenylamino)-1-pentanol;

(2S)-2-Amino-5-(5-methyl-2-nitrophenylthioxy)pentanoic acid;

$N^2$-Boc-2-amino-5-(5-methyl-2-nitrophenylamino)-1-phenyl-1-pentanol; and $N^3$-Boc-3-amino-6-(5-methyl-2-nitrophenylamino)-2-phenyl-2-hexanol.

In another aspect of the present invention is provided the use as regulators of cGMP or NO production of compounds of Formula I and pharmaceutically-acceptable salts or prodrugs thereof, wherein $R^5$ is a dinitro-substituted $C_6$–$C_{12}$-aryl, as defined below.

Representative of known compounds useful as regulators of cGMP or NO production is 2-amino-5-(2-nitrophenoxy)valeric acid.

This invention also discloses novel intermediates for the novel compounds of the instant invention, which intermediates have the formula, (II),

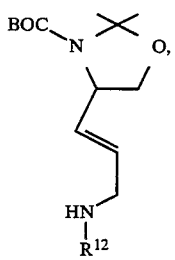

(II)

wherein $R^{12}$ is selected from the group consisting of:
(1) 5-methyl-2-nitrophenyl;
(2) 5-bromo-2-nitronaphthyl;
(3) 2,3-dimethyl-6-nitrophenyl;
(4) 5-chloro-2-nitrophenyl;
(5) 6-methyl-2-nitrophenyl;
(6) 3-methyl-2-nitrophenyl;
(7) 5-fluoro-2-nitrophenyl;
(8) 6-chloro-2-nitrophenyl;
(9) 5-chloro-2-nitrophenyl;
(10) 2,3-dichloro-6-nitrophenyl;
(11) 5-hydroxy-2-nitrophenyl; and
(12) 5-chloro-6-methyl-2-nitrophenyl.

"Alkenyl" refers to an "alkyl" radical of either from 2-to-6 ("$C_1$–$C_6$-alkenyl") or from 2-to-8 ("$C_1$–$C_8$-alkenyl") carbon atoms, which contains at least one carbon-carbon double bond.

"$C_1$–$C_4$-alkenylene" refers to a straight- or branched-chain diradical containing from 2-to-4 carbon atoms, for example, —CH=CH—, —C(CH$_3$)=CH—, —CH=CH—CH$_2$—, and the like.

"$C_2$–$C_4$-alkynylene" refers to a straight- or branched-chain diradical containing from 2-to-4 carbon atoms, for example, —C≡C—, —C≡C—CH$_2$—, —C≡C—CH(CH$_3$)—, —CH$_2$—C≡C—CH$_2$—, and the like.

"Alkoxy" and "thioalkoxy", as used herein, refer to $A^1$O— and $A^1$S— respectively, wherein $A^1$ is either a $C_1$–$C_4$-alkyl group or a $C_1$–$C_6$-alkyl group, as specified.

"Alkoxycarbonyl" refers to $A^2$O—C(O)—, wherein $A^2$ is a $C_1$–$C_4$-alkyl group, and includes, for example, methoxycarbonyl, ethoxycarbonyl, n-propyloxycarbonyl, isopropyloxycarbonyl, n-butyloxycarbonyl, isobutyloxycarbonyl and t-butyloxycarbonyl.

"Alkyl" refers to a straight- or branched-chain alkyl radical containing either from 1-to-4 carbon atoms ("$C_1$–$C_4$-alkyl") or from 1-to-6 carbon atoms ($C_1$–$C_6$-alkyl) including, but not limited, to methyl, ethyl, n-propyl, isopropyl, n-butyl, isobutyl, sec-butyl, n-pentyl, 2-methylbutyl, 2,2-dimethylpropyl, n-hexyl, 2-methylpentyl, 2,2-dimethylbutyl, n-hexyl, and the like.

"$C_1$–$C_3$-, $C_1$–$C_5$- or $C_1$–$C_4$-alkylene" refer to a straight- or branched-chain diradicals containing from the lower number to the larger number of carbon atoms indicated, for example, —CH$_2$—, —CH(CH$_3$)—, —(CH$_2$)$_4$—, and the like.

"$C_1$–$C_3$-alkylene-O-$C_1$–$C_3$-alkylene" refers to two $C_1$–$C_3$-alkylene groups, as defined above, linked by an oxygen atom, such as, for example, —CH$_2$—O—C(CH$_3$)$_2$—, —(CH$_2$)$_3$—O—CH$_2$—, —CH$_2$—O—CH$_2$, and the like.

"$C_1$–$C_3$-alkylene-phenylene" refers to a diradical containing the $C_1$–$C_3$-alkylene, as defined above, and the phenylene, as defined below, diradicals linked together in the order indicated, and connected to other groups at each end.

"Alksulfonyl" refers to $A^3$SO$_2$—, wherein $A^3$ is a $C_1$–$C_6$-alkyl group or a halo-$C_1$–$C_6$-alkyl group.

"$C_6$–$C_{12}$-aryl" or "$C_6$–$C_{12}$-aryl group", as used herein, refers to carbocyclic aromatic single or fused rings totaling 6-to-12 carbon atoms, for example, phenyl, naphthyl, indanyl, fluorenyl, terahydronaphthyl, indenyl, or isoindenyl.

"$C_6$–$C_{12}$-aryl-$C_1$–$C_4$-alkyl" refers to a $C_6$–$C_{12}$-aryl group, as defined above, appended to a $C_1$–$C_4$-alkyl radical, as defined above, including, but not limited to, benzyl, phenylethyl, naphthylmethyl and the like.

"$C_6$–$C_{12}$-aryloxy" as used herein refers to $A^4$O—, wherein $A^4$O— is a $C_6$–$C_{12}$-aryl group.

"$C_6$–$C_{12}$-arylsulfonyl" refers to $A^5$SO$_2$—, wherein $A^5$ is a $C_6$–$C_{12}$-aryl group, as defined above.

"Cyclo-$C_5$–$C_7$-alkenyl" refers to alicyclic unsaturated saturated ring having 5-to-7 carbon atoms, including but not limited to, cyclopentenyl, cyclohexenyl, and the like.

"Cyclo-$C_3$–$C_7$-alkyl" or "cyclo-$C_5$–$C_7$-alkyl" refer to alicyclic saturated ring shaving from 3-to-7 carbon atoms or 5-to-7 carbon atoms, respectively, including but not limited to, cyclopropyl, cyclobutyl, cyclopentyl, cyclohexyl, and the like.

"Cyclo-$C_5$–$C_7$-alkylene" refers to diradicals derived from cyclo-$C_5$–$C_7$-alkyl rings, as defined above, including but not limited to, cyclopentylene, cyclohexylene, cycloheptylene and the like.

"Cyclo-$C_5$-$C_7$-alkenylene" refers to diradicals derived from cyclo-$C_5$-$C_7$-alkenyl rings, as defined above, including but not limited to, cyclopentenylene, cyclohexenylene, and the like.

"1,4-Cyclo-$C_5$-$C_7$-alkylene" or "1,4-Cyclo-$C_5$-$C_7$-alkenylene" refer to a cyclo-$C_5$-$C_7$-alkylene diradical or a cyclo-$C_5$-$C_7$-alkenylene diradical, as defined above, which is linked to other groups at the 1- and 4-positions.

"Dinitro-substituted $C_6$-$C_{12}$-aryl" refers to a $C_6$-$C_{12}$-aryl group, as defined above, substituted at the 2-position with a nitro group, further substituted with an additional nitro group at a position other than the 4-position, and optionally further substituted, at a position other than the 4-position, with one or two substituents selected from $C_1$-$C_4$-alkyl, $C_1$-$C_4$-alkoxy, $C_1$-$C_4$-thioalkoxy, carboxy, carbo-$C_1$-$C_4$-alkoxy, cyano, halo-$C_1$-$C_4$-alkyl, hydroxy, amino, and $C_1$-$C_4$-alkylamino.

"Fused bi- or tricyclic carbocycle" refers to a fused ring attachment of the size indicated, such as, for example, indane, 1-indene, 4-indene, naphthyl, dihydronaphthyl, tetrahydronaphthyl, 1-fluorenyl, dihydro-1-fluorenyl, tetrahydro-1-fluorenyl, hexahydro-1-fluorenyl, 4-fluorenyl, dihydro-4-fluorenyl, tetrahydro-4fluorenyl, hexahydro-4-fluorenyl, and the like.

"Halogen", as used herein, refers to fluoro (F), chloro (Cl), bromo (Br) and iodo (I).

"Halo-$C_1$-$C_4$-alkyl", as used herein, refers to a $C_1$-$C_4$-alkyl radical, as defined above, in which one-to-three hydrogen atoms have been replaced by a halogen including, but not limited to, chloromethyl, 2-fluoroethyl, trifluoromethyl, and the like.

"Het", as used herein, refers to a 5- or 6-membered heterocyclic ring containing carbon atoms and one, two or three nitrogen atoms; one nitrogen and one sulfur atom; or one nitrogen and one oxygen atom; wherein the 5-membered ring has 0–2 double bonds and the 6-membered ring has 0–3 double bonds; wherein the nitrogen and sulfur heteroatoms may optionally be oxidized; and wherein the nitrogen heteroatom may optionally be quaternized. Such heterocycles include, but are not limited to, pyridyl, pyrimidinyl, furyl, thienyl, pyrazolyl, oxazolyl, isoxazolyl, 1,2,4-triazole, thiadiazole, tetrahydrofuryl, imidazolyl, piperazinyl, piperidinyl, pyrrolidinyl, thiazolyl, isoxazolinyl, and the like.

"Hydroxy-protecting group" or "oxygen-protecting group", as used herein, refers to a substituent which protects hydroxyl groups against undesirable reactions during synthetic procedures and includes, but is not limited to, substituted methyl ethers, for example, methoxymethyl, benzyloxymethyl, 2-methoxyethoxymethyl, 2-(trimethylsilyl)ethoxymethyl, benzyl, and triphenylmethyl; terahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates.

"N-Protecting group", "nitrogen-protecting group" or "N-protected", as used herein, refers to those groups intended to protect an amino group or the N-terminus of an amino acid or peptide against undesirable reactions during synthetic procedures or to prevent the attack of exopeptidases on the compounds or to increase the solubility of the compounds, and includes, but is not limited to, sulfonyl; acyl, such as acetyl, pivaloyl and benzoyl; alkoxycarbonyl, such as t-butyloxycarbonyl (Boc) and carbobenzyloxy (Cbz); and α-aminoacyl residues, which may themselves be similarly N-protected. Other intended groups may be found in Volume 3 of *The Peptides*, E. Gross and J. Meinhofer, editors, Academic Press, 1981.

"Pharmaceutically-acceptable ester" refers to the pharmaceutically-acceptable, nontoxic esters of the compounds of the present invention which include $C_1$-$C_6$-alkyl esters, wherein $C_1$-$C_6$-alkyl is as defined above, and $C_5$-$C_7$-cycloalkyl esters, wherein $C_5$-$C_7$-cycloalkyl refers to cyclic saturated hydrocarbon radicals, such as cyclopentyl, cyclohexyl, and the like. Also included are $C_6$-$C_{12}$-aryl-$C_1$-$C_6$-alkyl esters, wherein $C_6$-$C_{12}$-aryl-$C_1$-$C_6$-alkyl are as defined above. Representative examples include benzyl, phenethyl, and the like.

"Pharmaceutically-acceptable salts" refers to the pharmaceutically-acceptable, nontoxic, inorganic or organic acid addition salts of the compounds of the present invention, as described in greater detail on page 17 below.

"Phenylene", as used herein, refers to a phenyl diradical group, with the position of the connecting atoms being, 1,2-, 1,3- or 1,4-.

"Phenylene-$C_1$-$C_3$-alkylene" refers to a diradical containing the phenylene and the $C_1$-$C_3$-alkylene diradicals, as defined above, linked together in the order indicated, and connected to other groups at each end.

"Polypeptide chain", as used herein, refers to a series of from 1-to-6 amino acids joined by amide linkages which may be branched or linear, wherein the amino acids are selected independently from naturally-occurring amino acids, including but not limited to glycine, alanine, leucine, valine, phenylalanine, proline, methionine, tryptophan, asparagine, aspartic acid, glutamic acid, glutamine, serine, threonine, lysine, arginine, tyrosine, histidine, ornithine and the like.

The term "prodrug" refers to compounds that are rapidly transformed in vivo to yield the parent compounds of Formula (I), as for example, by hydrolysis in blood. T. Higuchi and V. Stella provide a thorough discussion of the prodrug concept in *Prodrugs as Novel Delivery Systems*, Vol. 14 of the A.C.S. Symposium Series, American Chemical Society (1975). Examples of esters useful as prodrugs for compounds containing carboxyl groups can be found on pages 14–21 of *Bioreversible Carriers in Drug Design: Theory and Application*, edited by E .B. Roche, Pergamon Press (1987).

The term "prodrug ester group" refers to any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art.

The term "protecting group" is well known in the art and refers to sustituents on functional groups of compounds undergoing chemical transformation which prevent undesired reactions and degradations during a synthesis; see, for example, T. H. Greene, *Protective Groups in Organic Synthesis*, John Wiley & Sons, (1981).

"Substituted $C_6$-$C_{12}$-aryl" refers to a $C_6$-$C_{12}$-aryl group, as defined above, substituted with one, two, or three substituents independently selected from $C_1$-$C_4$-alkyl, $C_1$-$C_4$-alkoxy, $C_1$-$C_4$-thioalkoxy, carboxy, carbo- $C_1$–$C_4$-alkoxy, cyano, halo-$C_1$–$C_4$-alkyl, hydroxy, amino, and $C_1$–$C_4$-alkylamino.

"Substituted-$C_6$–$C_{12}$-aryl-$C_1$–$C_4$-alkyl" refers to a substituted-$C_6$–$C_{12}$-aryl group, as defined above, appended to a $C_1$–$C_4$-alkyl radical, as defined above, including, but not limited to, 2-methylbenzyl, 4-chlorophenylethyl, 4-nitronaphthylmethyl, and the like.

"Substituted phenylene", as used herein, refers to a phenylene diradical, as define above, substituted with one or two substituents independently selected from the group consisting of (i) hydroxy, (ii) —$OR^{10}$, wherein $R^{10}$ is a hydroxy-protecting group, as defined above, (iii) amino, (iv) (N-protected)amino, as defined above, (v) halogen, (vi) oxo, (vii) $C_1$–$C_4$-alkoxy, (viii) $C_1$–$C_4$-thioalkoxy, (ix) $C_1$–$C_8$-alkenyl, (x) $C_6$–$C_{12}$-aryl-$C_1$–$C_6$-alkyl, (xi) cyclo-$C_3$–$C_7$-alkyl, (xi i) hydroxy-$C_1$–$C_4$-alkyl and (xiii) $C_1$–$C_3$-alkoxy-$C_1$–$C_4$-alkyl.

"Substituted $C_6$–$C_{12}$-arylsulfonyl" refers to a substituted $C_6$–$C_{12}$-aryl group, as defined above, appended to an —$SO_2$— radical.

By a "therapeutically-effective amount" of the compound of the invention is meant a sufficient amount of the compound to treat disorders, at a reasonable benefit/risk ratio applicable to any medical treatment. It will be understood, however, that the total daily usage of the compounds and compositions of the present invention is to be decided by the attending physician within the scope of sound medical judgement. The specific therapeutically-effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The following abbreviations are used herein: BOC or Boc for t-butyloxycarbonyl, Bz for benzyl, CBZ for benzyloxycarbonyl, $CDCl_3$ for deuterochloroform, $D_2O$ for deuterium oxide, DCC for dicyclohexylcarbodiimide, DIBAL for diisobutylaluminum hydride, DIEA for diisopropylethylamine, DMAP for dimethylaminopyddine, DMF for N,N-dimethylformamide, DMSO for dimethylsulfoxide, DMSO-$d_6$ for deuterodimethylsulfoxide, EDCl for 1-(3-dimethylaminopropyl)-3-ethylcarbodiimide hydrochloride, EtOH for ethanol, HOAc for acetic acid, IBCF for isobutyl chloroformate, LAH for lithium aluminum hydride, Ms for methanesulfonyl, $NH_4OAc$ for ammonium acetate, NMM for N-methylmorpholine and TEA for triethylamine, PAW for pyridine/acetic acid/water (20:6:11 ), TFA for trifluoroacetate, THF for tetrahydrofuran, and TMSi for trimethylsilyl.

Amino acids are herein designated as the natural L-isomer or as the D-isomer in accordance with convention, or chiral compounds, including amino acids, are assigned the R, S, or (B,S) configuration at the chiral center. Preferred compounds of the present invention are those which have the S configuration at the alpha-carbon atom, i.e. the carbon atom having substituents $R_4$ and Y. The terms "R" and "S" configuration used herein are as defined by IUPAC (IUPAC 1974 *Recommendations for Section E, Fundamental Stereochemistry, Pure Appl. Chem.*, 1976, 45: 13–30.)

The compounds of the present invention can be used in the form of pharmaceutically-acceptable salts derived from inorganic or organic acids. These salts include, but are not limited to, the following: acetate, adipate, alginate, aspartate, benzoate, benzenesulfonate, bisulfate, butyrate, camphorate, camphorsulfonate, citrate, cyclopentanepropionate, digluconate, dodecylsulfate, ethanesulfonate, flavianate, fumarate, glucoheptonate, glycerophosphate, hemisulfate, heptonate, hexanoate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, phosphate, picrate, pivalate, propionate, succinate, tartrate, thiocyanate, tosylate, and undecanoate.

Appropriate cationic salts are also readily prepared by conventional procedures such as treating an acid of formula I with an appropriate amount of base, such as an alkali or alkaline earth metal hydroxide e.g. sodium, potassium, lithium, calcium, or magnesium, or an organic base such as an amine, e.g., dibenzylethylenediamine, cyclohexylamine, dicyclohexylamine, triethylamine, piperidine, pyrrolidine, benzylamine, and the like, or a quaternary ammonium hydroxide such as tetramethylammonium hydroxide and the like. Also, the basic nitrogen-containing groups can be quaternized with such agents as loweralkyl halides, such as methyl, ethyl, propyl, and butyl chlorides, bromides, and iodides; dialkyl sulfates; long chain halides such as decyl, lauryl, myristyl, and stearyl chlorides, bromides and iodides; arylalkyl halides like benzyl and phenethyl bromides, and others. Water or oil-soluble or dispersible products are thereby obtained.

The salts of the present invention can be synthesized from the compounds of formula I which contain a basic or acidic moiety by conventional methods, such as by reacting the free base or acid with stoichiometric amounts or with an excess of the desired salt forming inorganic or organic acid or base in a suitable solvent or various combinations of solvents.

When a compound of formula (I) is used in a human subject, the total daily dose administered in single or divided doses may be in amounts, for example, from about 0.01 to about 50 mg/kg body weight, or more, usually, from about 0.2 to about 30 mg/kg body weight. Single dose compositions may contain such amounts or submultiples thereof to make up the daily dose. In general, treatment regimens according to the present invention comprise administering to a patient in need of such treatment from about 20 mg to about 2000 mg of the compound(s) of this invention per day in multiple doses or in a single dose.

The amount of active ingredient that may be combined with the carrier materials to produce a single dosage form will vary depending upon the host treated, the particular treatment and the particular mode of administration.

It will be understood, however, that the specific dose level for any particular patient will depend upon a variety of factors including the activity of the specific compound employed, the age, body weight, general health, gender and diet of the patient, the time of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically-acceptable carriers, adjuvants, and vehicles as desired. The term parenteral as used herein includes subcutaneous injections, intravenous, intramuscular, intrasternal injection, or infusion techniques.

Liquid dosage forms for oral administration may include pharmaceutically-acceptable emulsions, microemulsions, solutions, suspensions, syrups and elixirs containing inert diluents commonly used in the art such as water. Such compositions may also comprise adjuvants, such as wetting agents; emulsifying and suspending agents; and sweetening, flavoring and perfuming agents.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butandiol. Among the acceptable vehicles and solvents that may be employed are water, Ringer's solution, isotonic sodium chloride solution. In addition, sterile fixed oils are conventionally employed as a solvent or suspending medium. For this purpose any bland fixed oil may be employed including synthetic mono- or di-glycerides. In addition, fatty acids such as oleic acid find use in the preparation of injectables.

The injectable formulation can be sterilized, as for example by filtration through a bacteria-retaining filter, or by incorporating sterilizing agents in the form of sterile solid compositions which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include poly-orthoesters and polyanhydrides. The depot injectables can also be made by entrapping the drug in liposomes or microemulsions which are compatible with body tissues.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Dosage forms for topical or transdermal administration of a compound of this invention include ointments, pastes, creams, lotions, gels, powders, solutions, sprays, inhalants or patches. The active component is admixed under sterile conditions with a pharmaceutically-acceptable carrier and any needed preservatives or buffers as may be required. Ophthalmic formulations, ear drops, eye ointments, powders and solutions are also contemplated as being within the scope of this invention.

The present agents can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic physiologically acceptable and metabolizable lipid capable of forming liposomes can be used. The present compositions in liposome form can contain, in addition to the compounds of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Vol. XIV, Academic Press, New York, N.Y. 1976, pp. 33 et seq. The foregoing is merely illustrative of the invention and is not intended to limit the invention to the disclosed compounds. Variations and changes which are obvious to one skilled in the art are intended to be within the scope and nature of the invention which are defined in the appended claims.

The compounds of this invention may be administered alone or in combination or in concurrent therapy with other agents.

General Experimental Procedures for Bioassays

The enzyme NO synthase produces EDRF/NO and citrulline from L-arginine (Bredt and Snyder, *Proc. Nat'l Acad Sci USA*, 1989, 87: 682–5). The enzymatic generation of EDRF/NO is monitored by measuring the conversion of [$^3$H]-L-arginine to [$^3$H]-L-citrulline. An inhibitor of this specific enzymatic reaction lowers the conversion rate and, thus, the amount of [$^3$H]-L-citrulline produced. Likewise, a compound acting as a substrate would compete with L-arginine and thereby lower the conversion rate.

In those instances where it is suspected that the test substance is acting as a substrate rather than an inhibitor, the EDRF/NO may be estimated. For this confirmation bioassay, a method for quantification of endothelium-derived relaxing factor (EDRF) is utilized (first described in U.S. application Ser. No. 07/369,364, filed Jun. 21, 1989, now abandoned, and U.S. application Ser. No. 07/755,398, filed Sep. 5, 1991, now U.S. Pat. No. 5,288,897). This technique, measuring cyclic GMP responses of RFL-6 rat fetal lung fibroblast cells to estimate NO or EDRF is sensitive, simple and quite useful for the evaluation of compounds that regulate EDRF/NO release from various endothelial cells, or other cells or tissues (such as for example RAW cells (induced with LPS) and N1E-115 cells) [cf., Ishii, K., et al., *American Journal of Physiology*, 1991, 261:(2 pt 2) H598–603]. The cyclic GMP measured is an indirect measure of the amount of EDRF/NO produced by NO synthase, so compounds that reduce the amount of cyclic GMP produced are termed inhibitors of NO synthase, and those that increase cyclic GMP in the absence of exogenous L-arginine are termed substrates or stimulators of NO synthase.

Synthesis of the Compounds of the Invention

The compounds of the present invention may be synthesized by methods illustrated in Schemes I–VIII. In accordance with Scheme I, alpha, omega-diamino acids, suitable for use as starting materials, that are not commercially available are synthesized by reacting an amino alcohol of Formula 1 with a reagent such as ethyl trifluoroacetate to form the amino-protected compound of Formula 2. The hydroxyl group of this compound is oxidized to an oxo group to provide the compound of Formula 3, by treatment with DMSO and oxalyl chloride in TEA, for example. The oxo compound is then reacted with an amine and TMSiCN, followed by treatment with aqueous acid and heat to form the amino acid compound of Formula 4. Alternatively, amino acids may be prepared from ketones by the Strecker reaction or a modification of the same (P. K. Subramanian and R. W. Woodward, Synthetic Communications, 1986, 15: 337–342). Conversion of the free carboxyl group to the t-butyl ester in order to form the compound of Formula 5 is accomplished by treatment with isobutene and sulfuric acid.

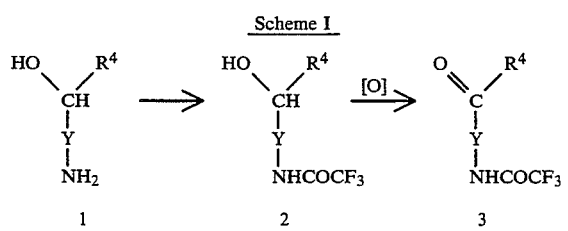

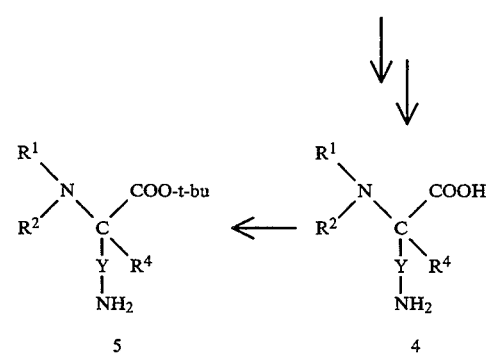

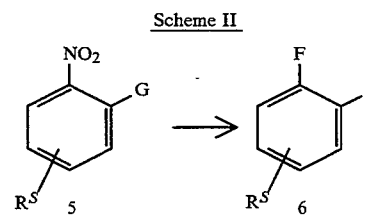

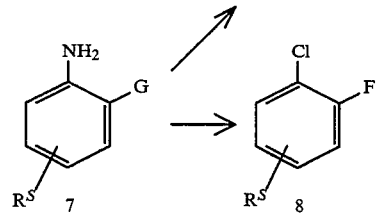

In accordance with Scheme II, wherein G is $NO_2$ or CN, the fluoro compound of Formula 6 or the chloro compound of Formula 8 is prepared. The dinitro compound of Formula 5 is reacted with, for example, tetrabutylammonium fluoride or potassium fluoride, to form the compound of Formula 6. Alternatively, an amino-nitro compound of Formula 7 is reacted with nitosonium tetrafluoroborate or sodium nitrite and pyridinium hydrofluoride to form compound 6, or with nitrous acid and CuCl to give the chloro compound of Formula 8.

In accordance with Scheme IIIa, the amine compound of Formula 4 is reacted with compound 6 or 8 in the presence of base to provide the compound of Formula 9, wherein $R^1$, $R^2$ and $R^3$ are as described for the compound of Formula I above, and R comprises the substituent or substituents described in the definition of substituted aryl above. In accordance with Scheme IIIb, in the specific instance wherein the amine group of the amino acid is substituted with a protecting group, such as a BOC or Cbz protecting group, the compound of Formula 4A is reacted with compound 6 or 8 in the presence of base to provide the compound of Formula 10 wherein $R^1$, $R^2$ and $R^3$ are as described for the compound of Formula I above, and R comprises the substituent or substituents described in the definition of substituted aryl above.

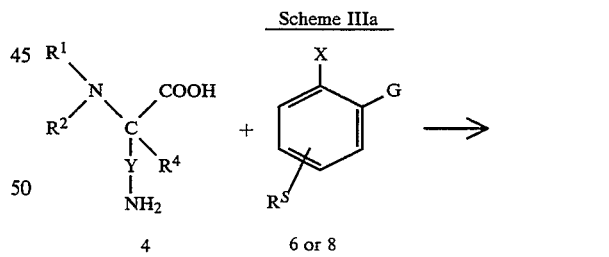

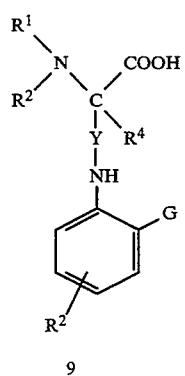

Scheme IIIb

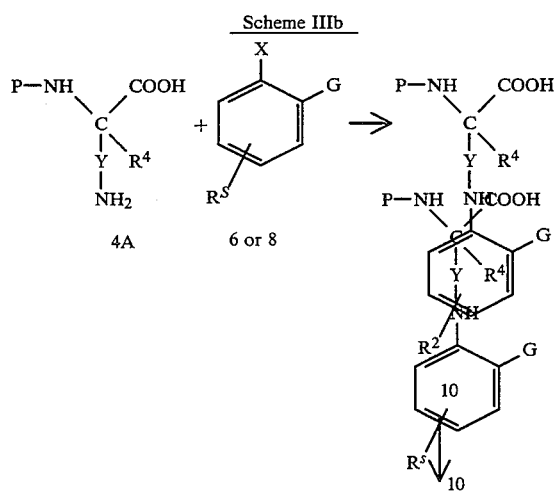

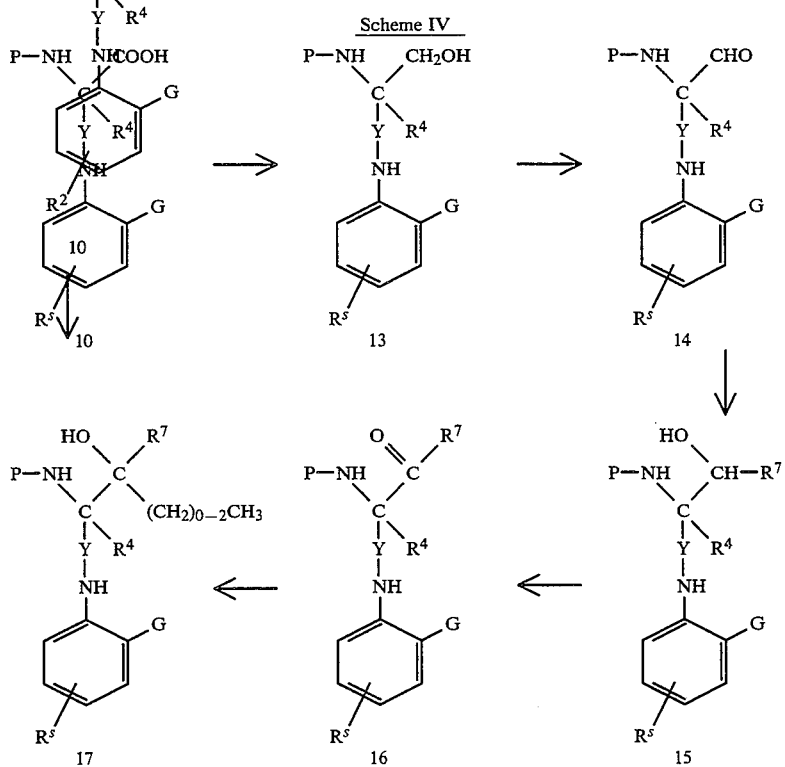

The compound of Formula 10 is reacted with DCC or another carbodiimide and a substituted amine to give the compound of Formula 11, which after removal of the protecting group gives the compound of Formula 12. Alternately, the compound of Formula 9 in Scheme IIIa may be reacted in a manner similar to that of compound 10 in Scheme IIIb to give analogs of compound 11. The procedures described are illustrative, and suitable analogs are easily determined by a skilled chemist.

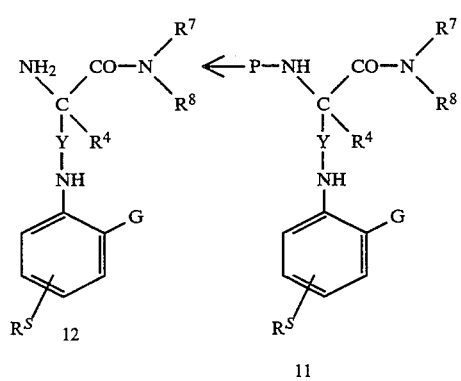

In accordance with Scheme IV, protected compounds of Formula 10 (or alternately compounds of Formula 9 from Scheme IIIa) are treated with a reducing agent, such as DIBAL or borane in THF to produce the alcohol of Formula 13. By treatment of compound 13 with an oxidizing agent, such as DMSO and oxalyl chloride in the presence of TEA at from 0° to −78° C., the aldehyde of Formula 14 is prepared. This compound in turn is reacted with a suitable alkylating reagent, such as for example an alkyl Grignard reagent under nitrogen and at a temperature of from −20° C. to −78° C. to produce the compound of Formula 15. By steps similar to those just described, the alcohol (15) is converted to the ketone of Formula 16 and the tertiary alcohol of Formula 17. The protecting group P can be removed from any of the compounds 10-17 by acidic hydrolysis, when the desired product is the deprotected analog of that compound.

Scheme V

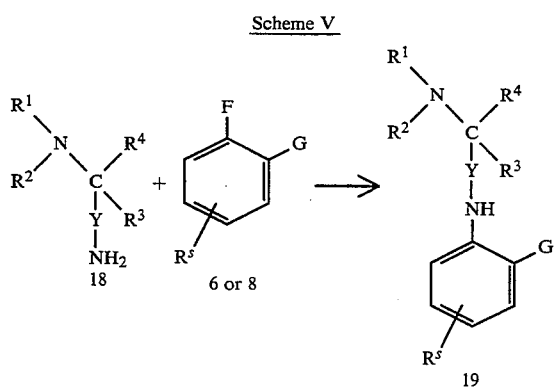

Scheme VI

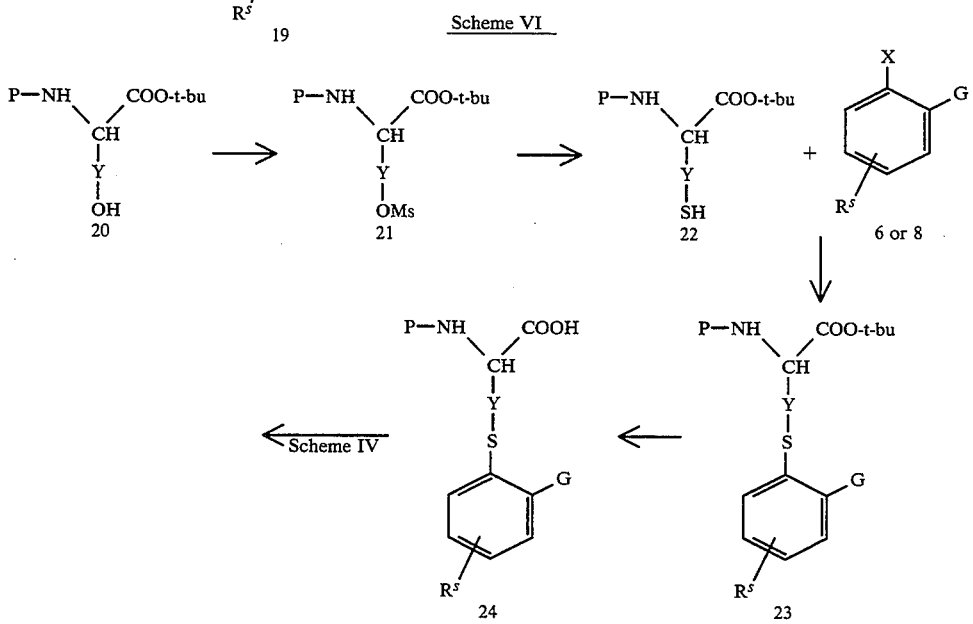

In accordance with Scheme V, in which the desired compound is a compound of Formula 1 wherein neither $R^3$ or $R^4$ is a carboxyl group or a derivative thereof, the substituted or protected amines of Formula 18 are reacted with compounds 6 or 8 to provide the compounds of Formula 19.

In accordance with Scheme VI, N-protected t-butyl esters of hydroxyamino acids of Formula 20, which are commercially available or prepared easily from the amino acids, are treated with methanesulfonyl chloride to form the mesylate compounds of Formula 21. In the instance where it is desired to prepare compounds of Formula I wherein Z is sulfur, the mesylate compound of Formula 21 is reacted with thiolacetic acid and potassium carbonate followed by treatment of the intermediate with ammonia to prepare the compound of Formula 22. This compound is condensed in the presence of base with compound 6 or 8 to form the compounds of Formula 23, which may be deprotected to the compounds 24, then carried forward, if desired, via Scheme IV to prepare additional examples within the scope of the present invention.

In accordance with Scheme VII is described the preparation of compounds of Formula I wherein $R^1$ is H and $R^3$ is hydroxymethylene or $-C(R^7)_2-OR^6$ etc., and $R^6$ and $R^7$ are as defined above. The compound of Formula 25, prepared as described in U.S. application Ser. No. 07/369,364, filed Jun. 21, 1989, now abandoned, is reacted with compound 6 or 8 to form the compound of Formula 26. Compound 26 is hydrolyzed with mild acid, such as acetic acid, to give the BOC-protected amino alcohol of Formula 27. Deprotection with stronger acid gives the amino alcohol 28, whereas oxidation, with for example Jones reagent, gives the BOC-protected amino acid of Formula 29. Compound 29 in turn may be substituted for the compound of Formula 10 in Schemes IIIb or IV, and carried forward as described above.

In accordance with Scheme VIII, aromatic amines of Formula 30 may be acetylated by the action of acetic anhydride to give compounds of Formula 31. The amides of Formula 31 may be nitrated with, for example, a mixture of nitric and sulfuric acids to give compounds of Formula 32. The amide group may be removed from compounds of Formula 32 by hydrolyzed with, for example, the

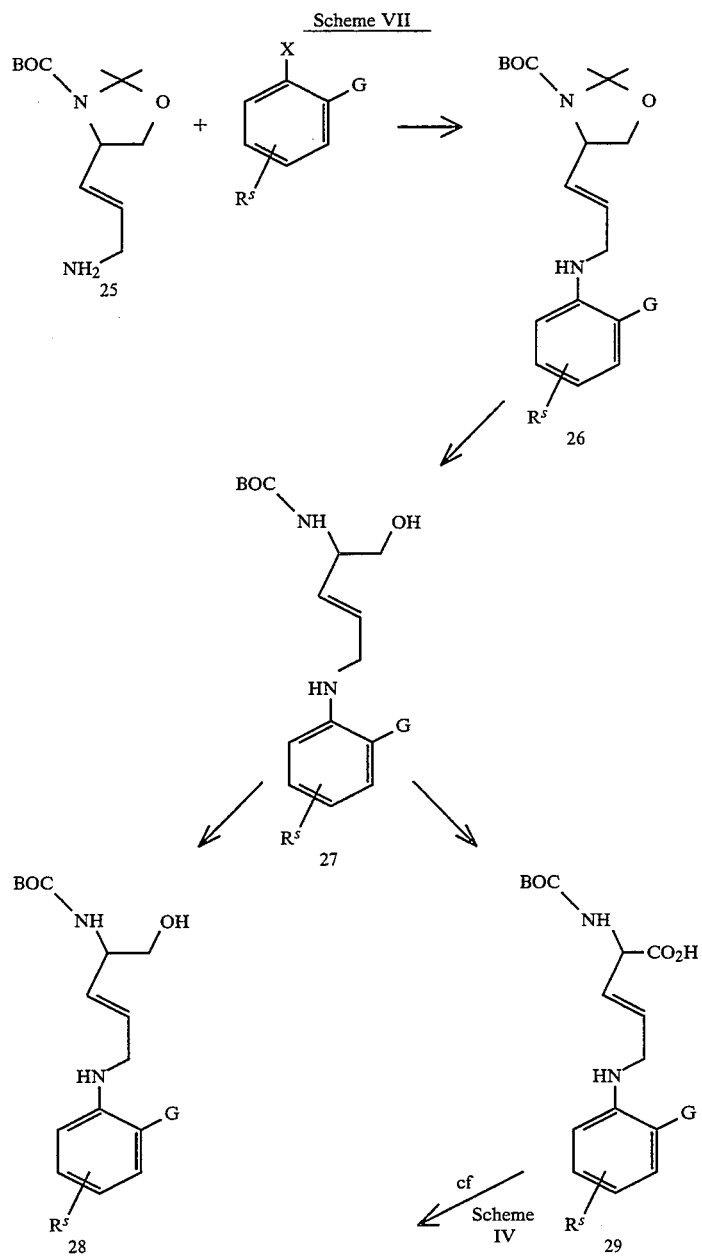

action of strong acid (70% sulfuric acid) or strong base (5N sodium hydroxide) The nitroaromatic compounds of Formula 33 may diazotized and the resulting diazoaromatics decomposed in the presence of a source of fluoride ion (following the procedure of D. J. Milner, *Synthetic Communications*, 1992, 22; 73–82) to prepare the fluoronitroaromatic compounds 34. Separately, cyanoamines of Formula 35 can be converted to 2-fluorocyanoaromatics compounds of formula 36 by diazotization followed by decomposition of the diazoaromatics in the presence of a source of fluoride ion as just described. The compounds 34 and 36 may be substituted for compound 6 or 8 of Schemes IIIa, IIIb, IV, or VII.

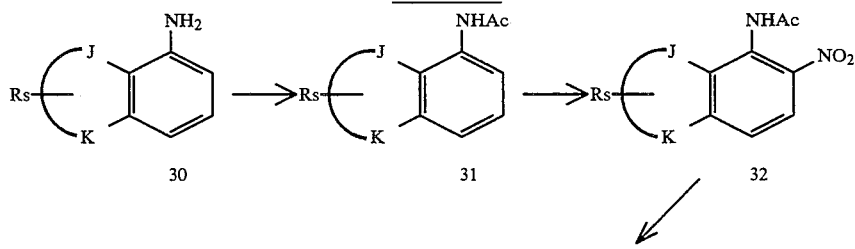

Scheme VIII

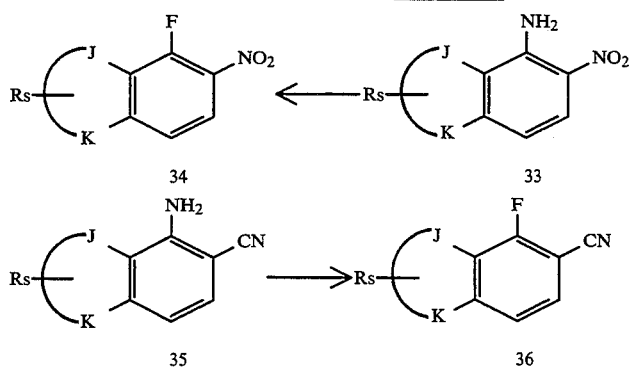

The following examples, which are provided for illustration and not limitation of the invention, will serve to further illustrate preparation of the novel compounds of the invention and biological activity thereof.

EXAMPLE 1

Biological Activity of Exemplified Compounds

[$^3$H]-arginine to [$^3$H]-H]-Citrulline Conversion

The conversion of L-arginine to L-citrulline was assayed as reported previously (Bredt and Snyder, Proc. Nat'l Acad Sci USA, 1989, 87: 682–5) with minor modifications. Briefly, samples of partially purified NO synthase, 50–100 mg of partially purified NO synthase or, alternately, 20 mL of a cytosolic preparation of NO synthase. The type 1 isoform of NO synthase was isolated from rat brain cerebellum cells partially purified on a phosphocellulose column. The cytosolic preparations of NO synthase (type II isoform) were prepared from RAW 264.7 cells (a murine monocyte-macrophage cell line), induced for 16 hours with 10 mg/mL medium of lipopolysaccharide (LPS). Another enzyme isoform (type III)is known to be present in bovine endothelial cells (BAE cells), and can be utilized if an additional assay is desired. The samples of enzyme were incubated for 20 minutes (3 minutes in the cases of purified enzyme preparations) at 25° C. in the presence of 10 mM L-[2,3-$^3$H]arginine (55 C$_i$/mmol) (containing 34 nM (0.2 mC$_i$)), 1 mM NADPH, 100 nM calmodulin, 2 mM CaCl$_2$, and with varying concentrations of inhibitors, in a final volume of 100 mL. The reaction was stopped by adding 1 mL of stop buffer (2 mM EGTA, 2 mM EDTA, 20 mM HEPES, pH 5.5). The total volume was then applied to a 1 mL Dowex AG 50WX-8 column (Na$^+$ form, BioRad) that had been pre-equilibrated with the stop buffer. L-[2,3-$^3$H]Citrulline was eluted (2×) with 0.5 mL of stop buffer and radioactivity was determined by liquid scintillation counting. The L-[2,3-$^3$H]arginine (Dupont, NEN) was purified prior to use on Dowex AG-1-X8 (CH$_3$CO$_2$— form, Bio-Rad), eluted with distilled water, acidified, concentrated on a Speed-Vac (Savant) and stored at −20° C. The data obtained for selected compounds of the present invention in the assay described above are given in Table 1.

TABLE 1

Inhibition of Type I (rat brain) and Type II (macrophage) NOS isoforms by substituted 2-nitrophenyl and 2-cycanophenyl compounds

| Compound from Example Number | Type I IC$_{50}$ μM | Type I % inhib. @ 100 μM | Type II IC$_{50}$ μM | Type II % inhib. @ 100 μM |
|---|---|---|---|---|
| NNLA* | 0.4 | 95 | 7 | 94 |
| 2 | 4 | 88 | 10 | 88 |
| 3 | 3 | 99 | 10 | nd |
| 4 | 3 | 94 | 2.5 | 99 |
| 5 | 20 | 68 | 100 | 46 |
| 6 | 100 | 55 | >100 | 11 |
| 7 | 40 | 91 | >100 | nd |
| 8 | 1 | 97 | 9 | 95 |
| 10 | 70 | 58 | 100 | 45 |
| 11 | >100 | 6 | 100 | 50 |

*L-NNA = Nγ-Nitro-L-arginine, a known NOS inhibitor used as a standard (cf M. A. Dwyer et al., Biochemical and Biophysical Research Communications, 1991, 176: 1136–1141 and K. Ishii et al., Canadian J. Physiol. Pharmacol., 1990, 68: 749–752).

EXAMPLE 2

(2S)-2-amino-5-(5-methyl-2-nitrophenylamino)pentanoic acid

A mixture of 474 mg (2 mmol) of Nα-BOC-L-ornithine (supplier BAChem) and 314 mg (2 mmol) of 3-fluoro-4-nitrotoluene (Aldrich Chemical Co.)in 2 mL of ethanol and 2 mL of 1N NaOH was heated at reflux for 12 hours. Another 2 mmol each of NaOH and 3-fluoro-4-nitrotoluene was added and the reaction was continued another two hours. The solution was poured into 50 mL of water and extracted with dichloromethane (2×80 mL). The organic phase was dried and concentrated to give a solid residue, which was stirred in 20 mL of 4N HCl in 33% acetic acid for four hours, filtered and concentrated to leave a yellow solid, which was recrystallized from ethanol/water to afford 296 mg (56% yield) of the title product as an amorphous orange powder. mp 263°–264° (decomp.); MS M/Z 268 [M+H], 285 [M+NH$_4$]; $^1$H NMR (300 MHz, D$_2$O/NaOD) δ: 1.64 (m, 4H)2.18 (s, 3H), 3.12 (m, 2H), 3.30 (t, J=4.5 Hz, 1H), 6.22 (d, J=8.1 Hz, 1H), 6.43 (s, 1H), 7.58 (d, J=8.1 Hz, 1H); $^{13}$C NMR (75.5 MHz, D$_2$O/NaOD) δ: 185.88, 158.28, 148.71, 130.81,128.71,120.22, 116.11, 58.73, 45.24, 35.40, 27.73, 24.24; Analysis calc'd for C$_{12}$H$_{17}$N$_3$O$_4$.0.4 HCl: C, 50.81; H, 6.25; N, 14.81; found: C, 50.79; H, 6.27; N, 14.73.

EXAMPLE 3

(2S)-2-amino-5-(5-methyl-2-nitrophenylamino)-pent-3E-en-1ol

Step 3a. (4S)-3-BOC-2,2-dimethyl-4-[3-(5-methyl-2-nitrophenylamino)-2-propenyl]-oxazolidine A 82 mg (0.32 mmol) sample of 3-(1,1-dimethylethyl)-(S)-4-(3-aminopropen-1,E-yl)-2,2-dimethyl-3-oxazolidinecarboxylate (prepared as described in Example 9h of U.S. application Ser. No. 07/755,398, filed Sep. 5, 1991) was heated with 3-fluoro-4-nitrotoluene (82 mg, 0.41 mmol) in 0.4 mL of N NaOH and 2 mL of ethanol for six hours, at which time an additional 0.41 mmol each of NaOH and 3-fluoro-4-nitrotoluene were added and the reaction continued for an additional 6 hours. The reaction was poured into 80 mL of dichloromethane, which was washed with water, dried over sodium sulfate and evaporated to leave a yellow oil. The oil was purified by flash chromatography (dichloromethane/2% triethylamine) to give 49 mg of a yellow glass. MS (DCl/NH$_3$) M/Z: 392 [M+H], 408 [M+NH$_4$].

Step 3b. (2S)-2-amino-5-(5-methyl-2-nitrophenylamino)-pent-3E-en-1-ol (A-82070)

The compound from Example 3a was stirred in 12 mL of 4N HCl in 33% acetic acid for 24 hours, which was then concentrated in vacuo. The residue was purified by flash chromatography (12:1:1, acetonitrile/water/acetic acid) to give (after lyophilization) 40 mg (50 % yield) of a hygroscopic orange powder. MS M/Z: 252 [M+H]. $^1$H NMR (300 MHz, D$_2$O) δ: 8:2.33 (s, 3H); 3.63 (dd, J=15, 7.5 Hz, 1H), 3.70 (dd, J=15, 4 Hz, 1H), 3.95 (m, 1H), 4.12 (d, J=3 Hz, 2H), 5.66 (dd, J=15, 6.3 Hz, 1H), 6.1 (dd, J=15, 4.5 Hz, 1H), 6.60 (d, J=7.8 Hz, 1H), 8.04 (d, J=7.8 Hz, 1H).

EXAMPLE 4

2-amino-5-(5-methyl-2-nitrophenylamino)-1-pentanol

A mixture of 2.37 g (10 mmol) of N$^\alpha$LBOC-L-ornithine (BAChem) and 1.65 g (11.0 mmol) of 3-fluoro-4-nitrotoluene in 10 mL of 1N NaOH and 10 mL of ethanol was heated at reflux for 48 hours, then cooled to room temperature. The reaction mixture was poured into 200 mL of dichloromethane and 200 mL of water and brought to pH 2 with 1N HCl and shaken. The dichloro methane extract was separated and dried over sodium sulfate. The organic extract was concentrated in vacuo to give an orange oil, N$^2$-BOC-N$^6$-(2-nitro-5-methylphenyl)-L-ornithine. A solution of 384 mg (1.05 mmole) of N$^2$-BOC-N$^6$-(2-nitro-5-methylphenyl)-L-ornithine in 4 mL of THF was cooled to 0° C. and a solution of borane in THF (1.31 mL of 1M, 1.31 mmole) was added dropwise two minutes. Evolution of gas followed, and the pale yellow solution gradually darkened over one hour. TLC showed incomplete reaction, so more (1.3 mL) borane-THF was added. After an additional hour, the reaction was quenched with 4 mL of methanol, and poured into 150 mL of dichloromethane and washed with 125 mL of water and dried (MgSO4). Concentration in vacuo gave a foam, which was purified on silica gel, eluting with 10% ethanol/dichloromethane. A yellow foam was obtained (89 mg). The yellow foam was dissolved in 21 mL of 33% acetic acid/4-N HCl and stirred for 12 hours. Concentration in vacuo gave a yellow powder which was recrystallized from ethanol/ethyl acetate to give 55 mg (15 %) of a yellow powder. m.p. 202°-204° (decomp.); $^1$H NMR (300 MHz, D$_2$O) δ: 8.00 (d, J=8.4 Hz, 1H), 6.82 (s, 1H), 6.55 (dd, J=8.4, 0.6 Hz, 1H), 3.35–3.45 (m, 3H), 2.33 (s, 3H), 1.80 (m, 4H); MS (FAB+) m/e calc'd for C$_{12}$H$_{20}$N$_3$O$_3$: 254.1505, found 254.1505; [M+H]$^+$ at 254; Analysis calc'd for C$_{12}$H$_{19}$N$_3$O$_3$.(2.8 HCl): C, 40.56; H, 6.18; N, 11.82; found: C, 40.67; H, 5.41; N, 11.67.

EXAMPLE 5

(2S)-2-amino-5-(5-methoxy-2-nitrophenylamino)pentanoic acid

Step 5a. 2-nitro-5-methoxy-fluorobenzene

To a solution of 2.30 g (14.6 mmole) of 3-fluoro-4-nitrophenol (Aldrich) and 2.26 mL (36.6 mmole) of iodomethane in 30 mL of DMF was added 4.04 g (2.93 mmole) of potassium carbonate. The mixture was stirred at room temperature for 16 hours, then poured into 250 mL of water and extracted with 250 mL of ether. Concentration in vacuo gave a yellow solid which was purified by sublimation to give 2.27 g (91%) of pale yellow crystals.: MS (DCl/NH$_3$) M/Z: 189 [M+NH$_3$], 224 [M+NH$_3$+2NH$_4$].

Step 5b. (2S)-2-amino-5-(5-methoxy-2-nitrophenylamino)pentanoic acid

A solution of 696 mg (3.0 mmol) of N$^\alpha$-BOC-L-ornithine and 513 mg (3 mmol) of 5-methoxy-2-nitrofluorobenzene in 3 mL of 1N NaOH and 3 mL of ethanol were heated at reflux for 20 hours, then concentrated in vacuo to a yellow oil. The oil was dissolved in 21 mL of 4N HCl in 33% acetic acid and stirred for 12 hours, then suspended in 50 mL of water and washed with 30 mL of dichloromethane and concentrated in vacuo to give a yellow powder. This was recrystallized twice from acetic acid/water to afford the title product as yellow crystals. mp 245°–246°; MS M/Z (DCl/NH$_3$) 284 [M+H]; $^1$H NMR (300 MHz, D$_2$O/NaOD) δ: 8:1.45 (m, 4H), 2.81 (m, 2H), 3.10 (d, J=1 Hz, 4.2H), 3.52 (d, J=3 Hz, 5.7H), 5.52 (d, J=1 Hz, 3.0H), 5.69 (m, 1H), 7.33 (dd, J=1, 8.4 Hz, 5.7H); $^{13}$C NMR (75.5 MHz, D$_2$O/NaOD) δ: 185.47, 168.65, 150.74, 131.00, 127.20, 108.64, 96.78, 58.48, 45.27, 35.37, 27.37; Analysis calc'd for C$_{12}$H$_{17}$N$_3$O$_5$.0.2 H$_2$O: C, 50.24; H, 6.11; N, 14.65; found: C, 50.09; H, 6.03; N, 14.60.

EXAMPLE 6

(2S)-2-amino-5-(2-chloro-6-nitrophenylamino)pentanoic acid

A mixture of 696 mg (3 mmol) of N$^\alpha$-BOC-L-ornithine and 1.152 g (6 mmol) of 2,3-dichloro-nitrobenzene in 3 mL of 1N NaOH and 6 mL of ethanol were heated at reflux for 3 days. Another 1.5 mL of 1N NaOH was added, and the reaction was continued for another 24 hours. The reaction was concentrated in vacuo to give an orange paste which was dissolved in 30 mL of 1:1:1 acetic acid/water/12N aqueous hydrochloric acid and stirred for 18 hours at room temperature. This was diluted with 50 mL of water, and the precipitate was filtered off and discarded. The supernatant was concentrated in vacuo and purified by flash chromatography, eluting with 6:1:1 acetonitrile/water/acetic acid to give 263 mg of an orange-red powder. This was recrystallized from water to afford 62 mg of the title product as a red-orange powder. mp 205°–297° (dec.); MS M/Z (FAB): 288 [M+H]; $^1$H NMR (300 MHz, D$_2$O/DCl) 8:1.8–2.0 (m, 4H), 3.42 (td, J=2, 6.6 Hz, 0.8BH), 7.11 (t, J=1 Hz, 7.8H), 7.76 (dd, J=1, 7.8 Hz, 1H), 8.02 (dd, J=1, 7.8 Hz, 1H); $^{13}$C NMR (75.5 MHz, D$_2$O/DCl) δ:

178.20, 142.08, 139.04, 138.88, 128.79, 127.57, 125.13, 54.46, 49.66, 28.95, 26.49; Analysis calc'd for $C_{11}H_{14}N_3O_4Cl.0.3$ HCl: C, 44.24; H, 4.75; N, 14.07; found: C, 44.17; H, 4.75; N, 13.69.

EXAMPLE 7

(2S)-2-amino-6-(2-nitro-5-methylphenylamino)hexanoic acid

A mixture of 2.37 g (10 mmol) of $N^\alpha$-BOC-L-lysine and 1.65 g (11.0 mmol) of 3-fluoro-4-nitrotoluene in 10 mL of 1N NaOH and 10 mL of ethanol were heated at reflux for 48 hours, then cooled to room temperature. A precipitate was filtered off and discarded. Removal of the solvent/n vacuo gave an oil which was dissolved in 50 % ethanol/3M $NH_3$ and taken to dryness. The residue was dissolved in 12 mL of 4N HCl in 33% acetic acid and stirred for four hours, then concentrated to dryness and purified by flash chromatography (eluting with 12:1:1 acetonitrile/water/HOAc). The resulting oil was recrystallized from water/methanol to afford 470 mg (42% yield) of the title product as bright orange prisms.: mp 234°-235° (dec.); MS M/Z (DCl/$NH_3$): 282 $[M+H]^+$; $^1H$ NMR (300 MHz, $D_2O$) δ: 1.1-1.45 (m, 6H), 2.78 (t, J=6.6 Hz, 2H), 2.99 (t, J=6.0 Hz, 1H), 5.88 (d, J=7.8 Hz, 1H), 6.07 (s, 1H), 7.32 (d, J=7.8 Hz, 1H). $^{13}C$ NMR (75.5 MHz, $D_2O$) δ: 185.73, 151.31,148.37, 131.02, 119.60, 116.09, 58.83, 45.20, 37.87, 31.19, 25.86; Analysis calc'd for $C_{13}H_{19}N_3O_4$: C, 55.51;H, 6.81;N, 14.94; found: C, 55.25;H, 6.94; N, 14.75.

EXAMPLE 8

2(S)-amino-5-(5-methyl-2-nitrophenylthioxy)pentanoic acid

Step 8a. 2(S)-Benzyloxycarbonylamino-5-(5-methylsulfonyloxy)pentanoic acid t-butyl ester To an oven dried flask under a nitrogen atmosphere was added a 4.65 g (14.40 mmol) sample of the t-Butyl ester of $N^\alpha$-CBZ-D-hydroxynorvaline (prepared as described by Kolasa and Miller, *J. Org. Chem.* (1990) 55, 1711–1721; Dolence and Miller, J. Org. Chem., (1991) 56, 492–499)in 25 mL of dichloromethane and the reaction was cooled to 0° C. To the flask was added triethylamine (2.18 g, 21.60 mmol) and methanesulfonyl chloride (2.05 g,18.00 mmol), and the reaction was stirred at 0° C. under nitrogen for one hour. The reaction was poured into 100 mL of methylene chloride and the organic layer was washed with 50 mL of each of water, cold 1N HCl, sat $NaHCO_3$, and brine, and the solvent was dried over $Na_2SO_4$. The solution was concentrated in vacuo to give a yellow oil. The oil was purified by chromatography on silica gel, eluting with hexane/ethyl acetate (1/1 ). Removal of the solvent afforded the title product as a colorless oil (yield 91%). MS (DCl/$NH_3$) M/Z: 402 (M+H), 419 (M+$NH_4$); $^1H$ NMR (300 MHz, $CDCl_3$) δ: 1.48 (s, 9H), 1.70-1.85 (m, 2H), 1.90-2.00 (m, 2H), 3.00 (s, 3H), 4.20-4.32 (m, 3H), 5.10 (s, 2H), 5.40 (d, 1H), 7.30-7.38 (m, 5H); $^{13}C$ NMR (300 MHz, $CDCl_3$) d 24.987, 27.897, 29.013, 37.291, 53.637, 66.911, 69.110, 82.530, 109.207, 128.027, 128.124, 128.464, 136.192, 155.620.

Step 8b. 2(S)-Benzyloxycarbonylamino-5-mercaptopentanoic acid t-butyl ester

To 485 mg (1.21 mmol) of 2(S)-benzyloxycarbonylamino)-5-(5-methylsulfonyloxy)pentanoic acid t-butyl ester (step 8a) was added 0.103 mL (1.45 mmol) of thiolacetic acid in 3 mL of tetrahydrofuran and 200 mg (1.45 mmol) of potassium carbonate. The reaction was stirred at room temperature for six hours, then an additional 0.103 mL of thiolacetic acid and 200 mg of potassium carbonate were added and stirring continued for 12 more hours. The thiolesters were hydrolyzed by adding 5 mL of THF, 3 mL of 14.7M aqueous ammonium hydroxide and 5 mL of water. After 15 minutes at room temperature, the solution was poured into 80 mL of water and made acidic with 12N HCl. The residue was extracted with dichloromethane, washed with saturated sodium bicarbonate solution, and concentrated in vacuo to give a waxy solid which was used without further purification. MS M/Z (DCl/$NH_3$): 357 $[M+NH_4]$.

Step 8c. (S)-2-amino-5-(5-methyl-2-nitrophenylthioxy)pentanoic acid

A mixture of (2S)-t-butyl-N-carbobenzyloxy-2-amino-5-mercapto-pentanoate (156 mg, 0.46 mmoles, from step 8a) and 107 mg (0.69 mmoles) of 5-methyl-2-nitro-fluorobenzene in 0.69 mL of 1N NaOH and 2 mL of ethanol was heated at reflux for one hour. The reaction was poured into 120 mL of water and extracted with 80 mL of dichloromethane. Concentration of the dichloromethane layer in vacuo gave a yellow powder. The yellow powder was dissolved in 10 mL of 1M HBr in acetic acid and stirred for 60 hours hours at room temperature. Removal of solvent gave a thick yellow oil. Purification by flash chromatography eluting with 10:5:1:1 ethanol/ether/acetic acid/water gave two fractions (Rf=0.47(88 mg) and 0.51 (118 mg) ). The lower rf fraction was recrystallized from boiling water to give a fluffy yellow mass. TLC and PMR experiments proved that the two samples were different salt forms, with the samples displaying equivalent behavior in aqueous hydrochloric acid solutions: mp (of the rf=0.51 salt) 212°-214° C. (dec.); MS (FAB) M/Z: 285 $[M+H]$; $^1H$ NMR (300 MHz, $D_2O$/DCl) δ: 5:1.7-1.9 (m, 2H), 2.1-2.2 (m, 2H), 3.3 (t, J=2 Hz, 7.5H), 2.42 (s, 3H), 4.05 (t, J=1 Hz, 6H), 7.19 (d, J=1 Hz, 8.7H), 7.37 (s, 1H), 8.2 (d, J=1 Hz, 8.7H).

EXAMPLE 9

(2 R )-2-( N-(1,1-dimethylethoxycarbonyl)amino)-5-(5-methyl-2-nitrophenylamino)pentanoic acid To 696 mg (3.0 mmol) of Boc-D-Ornithine (as a 1M solution in ethanol) was added 551.5 mg (3.30 mmol) of 2-fluoro-3-nitrotoluene and 3 ml (3 mmol) of 1N sodium hydroxide. The reaction was heated to reflux for 24 hours. The reaction was concentrated/n vacuo. The product was purified by flash chromatography with acetonitrile/acetic acid/water 6/1/1. The product (620 mg, 61% yield) was obtained was a yellow oil. mp>258° C. (dec.). MS (FAB) M/Z: 268 (M+H). $^1H$ NMR (300 MHz, $CDCl_3$) δ: 1.7-2.0 (m, 4H), 2.1 (s, 9H), 2.45 (s, 3H), 3.40 (t, 2H), 4.00 (t, 1H), 6.60 (td, 1H), 7.10 (dd, 1H), 8.00 (dd, 1H).

EXAMPLE 10

(2R)-2-amino-5-(5-methyl-2-nitrophenylamino)pentanoic acid A82583

To 550 mg (1.5 mmol) of (2R)-2-BOC-amino-5-(5-methyl-2-nitrophenylamino)pentanoic acid was added an excess of aqueous HCl in HOAc. The reaction was stirred for 3 hours and concentrated/n vacuo. The product was purified by flash chromatography with acetonitrile/acetic acid/water 6/1/1. The product (375 mg, 95% yield) was obtained as a yellow solid. mp >285° C. (dec.); MS (DCl/NH3) M/Z: 268 (M+H); $^1$H NMR (300 MHz, D$_2$O) δ: 1.7–2.2 (m, 4H), 2.42 (s, 3H), 3.55 (t, 2H), 4.02 (t, 1H), 6.95 (d, 1H), 7.25 (s, 1H), 8.2 (d, 1H).

EXAMPLE 11

(2S)-2-amino-5-(2-cyanophenylamino)pentanoic acid

A solution of 928 mg (4 mmoles) of N$^α$-Boc-L-ornithine and 968 mg (8 mmoles) of 2-fluorobenzonitrile in 4 mL of ethanol and 4 mL of 1N NaOH were heated at reflux for 24 hours. Another 8 mmoles each of 1N NaOH and 2-fluorobenzonitrile were then added and reflux was continued for another 24 hours. The clear solution was cooled to room temperature, and the white paste dumped into 125 mL of CH$_2$Cl$_2$ and extracted with 100 mL of water made basic (pH 12) with NaOH. The aqueous extract was acidified with 5N HCl, and extracted with 125 mL of CH$_2$Cl$_2$. The organic phase was washed with 1M HCl, dried (Na$_2$SO$_4$) and concentrated in vacuo to give an oil. The oil was purified by flash chromatography on silica gel, eluting with 2:1 ethyl acetate:ethanol containing 1% triethylamine. The sole fluorescent product was an oil, 132 mg (10%), with rf of 0.49 in the elution solvent. 125 mg of the oil was dissolved in 22 mL of 5:1:1 acetic acid/water/12M HCl, and stirred for 3 hours at room temperature. The sample was concentrated in vacuo, then ethanol was added and the sample again concentrated in vacuo to give a waxy solid. This was recrystallized from water to give 22.5 mg of white needles. The mother liquor yielded 67 mg of white foam on concentration. Yield (100%).: mp >265°; MS (FAB) m/e calc'd for C$_{12}$H$_{10}$N$_3$O$_2$: 234.1243, found 234.1231; M/Z 223 (M+), 224 (M+H)$^+$. $^1$H NMR (300 MHz, D$_2$O) δ: 1.74 (m, 2H), 1.96 (m, 2H), 3.33 (t, J=6.0 Hz, 2H), 3.79 (t, J=5.8 Hz, 1H), 6.71 (t, J=7 Hz, 1H), 6.92 (d, J=9 Hz, 1H), 7.55 (m, 1H).

EXAMPLE 12

2 (S)-amino-5-(5-methyl-2-nitrophenylthioxy)pentanol

Step 12a. 2(S)-Benzyloxycarbonylamino-5-(5-methylamino-5-(5-methyl-2-nitrophenylthioxy)pentanoic t-butyl ester A mixture of 0.5 mmol of 2(S)-benzyloxycarbonylamino-5-thioxypentanoic acid t-butyl ester (from example 8b) and 0.75 mmol of 5-methyl-2-nitrofluorobenzene in 0.69 mL of 1N NaOH and 2 mL of ethanol is heated at reflux for one hour. The reaction is poured into 120 mL of water and extracted with 80 mL of dichloromethane. Removal of the solvent in vacuo affords the title product.

Step 12b. 2(S)-Benzyloxycarbonylamino-5-(5-methyl-2-nitrophenylthioxy)pentanoic acid The crude material from step 12a is selectively hydrolyzed to remove the t-buty ester group by dissolving the material in 0.5N HBr/50% aqueous ethanol and stirring for 1 hour. The solvent and excess acid are removed in vacuo, and the crude product is taken directly to the next step.

Step 12C. 2(S)-Benzyloxycarbonylamino-5-(5-methyl-2-nitrophenylthioxy)pentanol

A solution of 0.5 mmol of the free acid from step 12b above, in 4 mL of THF is cooled to 0° C. and 0.8 mL of 1M borane in THF (0.8 mmol) is added dropwise over two minutes with stirring. After one hour an additional 0.8 mL of borane in THF is added and the reaction is stirred an additional hour. The reaction is quenched with 4 mL of methanol, and the mixture is poured into 150 mL of dichloromethane, which is washed with 125 mL of water and dried (MgSO4). After concentration in vacuo and chromatography on silica gel, the product is obtained.

Step 12d. 2(S)-amino-5-(5-methyl-2-nitrophenylthioxy)-pentanol

The product of step 12c is dissolved in 10 mL of 1M HBr in acetic acid, and the solution is stirred for 60 hours at room temperature. Removal of the reagent and solvent by evaporation and purification by chromatography on silica gel yields the title product.

EXAMPLE 13

N$^2$-Boc-2-amino-5-(5-methyl-2-nitrophenylamino)-1-phenyl-1-pentanol

Step 13a. N$^2$-Boc-2-amino-5-(5-methyl-2-nitrophenylamino)-1-pentanol 2-amino-5-(5-methyl-2-nitrophenylamino)-1-pentanol (10 mmol) from example 4 is treated with an equivalent of di-t-butyldicarbonate in the presence of one equivalent of base (triethylamine) in methylene chloride at 0° C. The product mixture is taken up in ethyl acetate and water and the ethyl acetate mixture is separated and washed successively with dilute aqueous hydrochloric acid, sodium bicarbonate solution, and then dried over magnesium sulfate. The solution is filtered and concentrated. Chromatography of the residue provides product.

Step 13b. N$^2$-Boc-2-amino-5-(5-methyl-2-nitrophenylamino)-1-pentanal

The product of step 13a is added in solution to a mixture of one equivalent of DMSO and one equivalent of oxalyl chloride, pre-prepared at −78° C. according to the method of Swern. One equivalent of tertiary amine base is added (N-ethyldiisopropylamine). After several minutes (30–45) a second equivalent of base is added and the reaction mixture slowly warmed to 0° C. After stirring at 0° C. for 20 minutes the mixture is partitioned between ethyl acetate and water. The ethyl acetate extract is washed with dilute hydrochloric acid and then with sodium bicarbonate solution and dried over sodium sulfate. The solution is filtered and concentrated and can be used directly or purified further by chromatography if necessary.

Step 13c. N$^2$-Boc-2-amino-5-(5-methyl-2-nitrophenylamino)-1-phenyl-1-pentanol

To a mixture of the product from step 13b stirring in THF at 0° C. is added 2 equivalents of phenyl magnesium bromide. The reaction is stirred for several hours and methanol slowly added with cooling to destroy unreacted phenyl magnesium bromide. The mixture is taken up in ammonium chloride solution and ethyl acetate. The ethyl acetate extract is separated, washed with ammonium chloride solution and saturated sodium bicarbonate solution, and dried over magnesium sulfate. The solution is filtered and concentrated and the residue purified by chromatography to provide the product.

EXAMPLE 14

N$^2$-Boc-2-amino-5-(5-methyl-2-nitrophenylamino)-1-phenyl-1-pentanone

The product of step 13c is treated according to the same sequence as in step 13b to provide desired product.

EXAMPLE 15

$N^3$-Boc-3-amino-6-(5-methyl-2-nitrophenylamino)-2-phenyl-2-hexanol

The product of step 14 is treated with methyl lithium (2 equivalents) and magnesium bromide (1 equivalent) in diethyl ether solution in a similar manner as in step 13c to provide desired product.

EXAMPLE 16

$N^2$-Hexanoyl-(2S)-2-amino-5-(5-methyl-2-nitrophenylamino)pentanoic acid

A sample of (2S)-2-amino-5-(5-methyl-2-nitrophenylamino)pentanoic acid (the product of example 2) is reacted with hexanoyl chloride at 5° C. in water/dioxane solvent with the pH being maintained at 8.5 –9.5 by the addition of sodium hydroxide solution. When the reaction is complete by tlc the reaction mixture was acidified to pH 2.0 and is then partitioned between ethyl acetate and water. The aqueous mixture is extracted with two portions of ethyl acetate and the combined ethyl acetate extracts are extracted with water and dried over sodium sulfate. The solution is filtered, concentrated and the residue purified by chromatography to provide product.

EXAMPLE 17

$N^2$-Hexanoyl-(2S)-2-amino-5(5-methyl-2-nitrophenylthioxy)pentanoic acid

A sample of (2S)-2-amino-5-(5-methyl-2-nitrophenylthioxy)pentanoic acid (the product of example 8) is reacted with hexanoyl chloride as in example 16 to provide the title product.

EXAMPLE 18

2-amino-5-(5-methyl-2-nitrophenylamino)-1-phenyl-1-pentanol

A sample of $N^2$-Boc-2-amino-5-(5-methyl-2-nitrophenylamino)-1-phenyl-1-pentanol (the product of example 13, step c) is reacted with aqueous HCl in HOAc as in example 10 to provide the title product.

EXAMPLE 19

3-amino-6-(5-methyl-2-nitrophenylamino)-2-phenyl-2-hexanol

A sample of $N^3$-Boc-3-amino-6-(5-methyl-2-nitrophenylamino)-2-phenyl-2-hexanol (the product of example 15) is reacted with aqueous HCl in HOAc as in example 10 to provide the title product.

EXAMPLE 20

4-(5-methyl-2-nitrophenylamino)phenyl-(S)-glycine

In place of N-BOC-L-ornithine, a sample of N-BOC-p-aminophenyl-(S)glycine (from BAChem) is reacted with 3-fluoro-4-nitrotoluene following the procedure of example 2 to provide the title product.

EXAMPLES 21–31

Following the procedure of Example 16, substituting the reagent shown for 25 the hexanoyl chloride of Example 16, the products of Examples 21–31 are produced as shown in Table 2.

TABLE 2

| Example number | Reagent | Product |
|---|---|---|
| 21 | Benzoyl chloride | $N^2$-Benzoyl-2(S)-amino-5-(5-methyl-2-nitrophenylamino)pentanoic acid |
| 22 | Acetyl chloride | $N^2$-acetyl-2(S)-amino-5-(5-methyl-2-nitrophenylamino)pentanoic acid |
| 23 | Phenylacetyl chloride | $N^2$-Phenylacetyl-2(S)-amino-5-(5-methyl-2-nitrophenylamino)pentanoic acid |
| 24 | Trifluoroacetic anhydride | $N^2$-Trifluoroacetyl-2(S)-amino-5-(5-methyl-2-nitrophenylamino)pentanoic acid |
| 25 | Cinnamyl chloride | $N^2$-(4-Phenyl-2E-butenoyl)-2(S)-amino-5-(5-methyl-2-nitrophenylamino)pentanoic acid |
| 26 | trans-Crotonyl chloride | $N^2$-(2E-Butenoyl)-2(S)-amino-5-(5-methyl-2-nitrophenylamino)pentanoic acid |
| 27 | Isobutyryl chloride | $N^2$-(2-Methylpropanoyl)-2(S)-amino-5-(5-methyl-2-nitrophenylamino)pentanoic acid |
| 28 | 2-Furoyl chloride | $N^2$-(2-Furoyl)-2(S)-amino-5-(5-methyl-2-nitrophenylamino)pentanoic acid |
| 29 | Cyclohexanecarboxylic acid chloride | $N^2$-(Cyclohexanecarbonyl)-2(S)-amino-5-(5-(methyl-2-nitrophenylamino)pentanoic acid |
| 30 | 2-Thiopheneacetyl chloride | $N^2$-(Thiopheneacetyl)-2(S)-amino-5-(5-methyl-2-nitrophenylamino)pentanoic acid |
| 31 | Cyclopropane carboxylic acid chloride | $N^2$-(Cyclopropanecarbonyl)-2(S)-amino-5-(5-(methyl-2-nitrophenylamino)pentanoic acid |

EXAMPLES 32–42

Following the procedure of Example 17, substituting the reagent shown for the hexanoyl chloride of Example 16, the products of Examples 32–42 are produced as shown in Table 3.

TABLE 3

| Example number | Reagent | Product |
|---|---|---|
| 32 | Benzoyl chloride | $N^2$-Benzoyl-2(S)-amino-5-(5-methyl-2-nitrophenylthioxy)pentanoic acid |
| 33 | Acetyl chloride | $N^2$-acetyl-2(S)-amino-5-(5-methyl-2- |

TABLE 3-continued

| Example number | Reagent | Product |
|---|---|---|
| | | nitrophenylthioxy)pentanoic acid |
| 34 | Phenylacetyl chloride | $N^2$-Phenylacetyl-2(S)-amino-5-(5-methyl-2-nitrophenylthioxy)pentanoic acid |
| 35 | Trifluoroacetic anhydride | $N^2$-Trifluoroacetyl-2(S)-amino-5-(5-methyl-2-nitrophenylthioxy)pentanoic acid |
| 36 | Cinnamyl chloride | $N^2$-(4-Phenyl-2E-butenoyl)-2(S)-2-amino-5-(5-methyl-2-nitrophenylthioxy)pentanoic acid |
| 37 | trans-Crotonyl chloride | $N^2$-(2E-Butenoyl)-2(S)-amino-5-(5-methyl-2-nitrophenylthioxy)pentanoic acid |
| 38 | Isobutyryl chloride | $N^2$-(2-Methylpropanoyl)-2(S)-amino-5-(5-methyl-2-nitrophenylthioxy)pentanoic acid |
| 39 | 2-Furoyl chloride | $N^2$-(2-Furoyl)-2(S)-amino-5-(5-methyl-2-nitrophenylthioxy)pentanoic acid |
| 40 | Cyclohexane carboxylic acid chloride | $N^2$-(Cyclohexanecarbonyl)-2(S)-amino-5-(5-methyl-2-nitrophenylthioxy)pentanoic acid |
| 41 | 2-Thiopheneacetyl chloride | $N^2$-(Thiopheneacetyl)-2(S)-amino-5-(5-methyl-2-nitrophenylthioxy)pentanoic acid |
| 42 | Cyclopropane carboxylic acid chloride | $N^2$-(Cyclopropanecarbonyl)-2(S)-amino-5-(5-methyl-2-nitrophenylthioxy)pentanoic acid |

EXAMPLES 45-52

Following the procedures of Example 13 and Example 10, reacting the $N^2$-Boc-2-amino-5-(5-methyl-2-nitrophenylamino)-1-pentanal of step 13b with the reagents shown substituting for the phenyl magnesium bromide of example 13c, and hydrolyzing the protecting group as in Example 10, the products of Examples 43-52 are prepared as shown in Table 4.

EXAMPLES 53-62

The products of Examples 43-52 are protected by the procedure of Example 13a, oxidized by the procedure of Example 13b, alkylated by the procedure of Example 15, deprotected by removal of the protecting group according to the procedure of Example 10, to produce the products of Examples 53-62, as shown in Table 5.

TABLE 4

| Example number | Reaaent | Product |
|---|---|---|
| 43 | Methyl magnesium bromide | 3-amino-6-(5-methyl-2-nitrophenylamino)-2-hexanol |
| 44 | Vinyl magnesium bromide | 4-amino-7-(5-methyl-2-nitrophenylamino)-1-hepten-3-ol |
| 45 | Ethyl magnesium bromide | 4-amino-7-(5-methyl-2-nitrophenylamino)-3-heptanol |
| 46 | Isobutyl magnesium bromide | 5-amino-8-(5-methyl-2-nitrophenylamino)-2-methyl-4-octanol |
| 47 | Allyl magnesium bromide | 5-amino-8-(5-methyl-2-nitrophenylamino)-1-octen-4-ol |
| 48 | Butyl magnesium bromide | 6-amino-9-(5-methyl-2-nitrophenylamino)-5-nonanol |
| 49 | Phenyl magnesium bromide | 2-amino-5-(5-methyl-2-nitrophenylamino)-1-phenyl-1-pentanol |
| 50 | 2-Thienyl lithium bromide | 2-amino-5-(5-methyl-2-nitrophenylamino)-1-(2'-thienyl)-1-pentanol |
| 51 | Cyclopentyl magnesium bromide | 2-amino-5-(5-methyl-2-nitrophenylamino)-1-(cyclopentyl)-1-pentanol |
| 52 | Cyclohexyl magnesium bromide | 2-amino-5-(5-methyl-2-nitrophenylamino)-1-(cyclohexyl)-1-pentanol |

TABLE 5

| Example number | Starting material from Example Number | Product |
|---|---|---|
| 53 | 43 | 3-amino-6-(5-methyl-2-nitrophenylamino)-2-methylhexanol |
| 54 | 44 | 4-amino-7-(5-methyl-2-nitrophenylamino)-3-methyl-l-hepten-3-ol |
| 55 | 45 | 4-amino-7-(5-methyl-2-nitrophenylamino)-3-methyl-3-heptanol |
| 56 | 46 | 5-amino-8-(5-methyl-2-nitrophenylamino)-2,4-dimethyl-4-octanol |
| 57 | 47 | 5-amino-8-(5-methyl-2-nitrophenylamino)-4-methyl-2-octen-4-ol |
| 58 | 48 | 6-amino-9-(5-methyl-2-nitrophenylamino)-5- |

TABLE 5-continued

| Example number | Starting material from Example Number | Product |
|---|---|---|
| | | methyl-5-nonanol |
| 59 | 49 | 3-amino-6-(5-methyl-2-nitrophenylamino)-2-phenyl-2-hexanol |
| 60 | 50 | 3-amino-6-(5-methyl-2-nitrophenylamino)-2-(2-thienyl)-2-hexanol |
| 61 | 51 | 3-amino-6-(5-methyl-2-nitrophenylamino)-2-(cyclopentyl)-2-hexanol |
| 62 | 52 | 3-amino-6-(5-methyl-2-nitrophenylamino)-2-(cyclohexyl)-2-hexanol |

EXAMPLES 63–67

Fluorination method A. 1-Fluoro-2-nitronaphthalene

To a well stirred slurry of nitrosonium tetrafluoroborate (Aldrich) (10 % molar excess, (cf. David J. Milner, *Synthetic Communications* (1992) 22 (1), 73–82.)) in dichloromethane at 0° C. is added 1-amino-2-nitronaphthalene. After 30 minutes, ortho-dichlorobenzene is added and the dichloromethane is distilled off, and the dichlorobenzene is heated at 50°–200 ° C. to decompose the diazonium tetrafluoroborate. Removal of solvent and purification of the product by chromatography or crystallization yields 1-fluoro-2-nitronaphthalene.

Following the procedure of the Fluorination Method A above, replacing the 1-amino-2-nitronaphthalene of that example with the starting material shown below, the corresponding fluoro compounds are prepared, which are then reacted with 3-(1,1-dimethylethyl)-(S)-4-(3-aminopropen-1,E-yl)-2,2-dimethyl-3-oxazolidinecarboxylate according to the procedure of Example 3, in order to prepare the products of Examples 63–67 are prepared as shown in Table 6.

TABLE 6

| Example number | Starting material | Product |
|---|---|---|
| 63 | 1-amino-5-bromo-2-nitronaphthalene | (2S)-amino-5-(2-nitro-5'-bromonaphthylamino)-pent-3E-enol |
| 64 | 2,3-dimethyl-6-nitro-aniline | (2S)-amino-5-(2,3-dimethyl-6-nitro-phenylamino)-pent-3E-enol |
| 65 | 5-chloro-2-nitro-aniline | (2S)-amino-5-(5-chloro-2-nitro-phenylamino)-pent-3E-enol |
| 66 | 2-amino-3-nitro-toluene | (2S)-amino-5-(2-nitro-6-methyl-phenylamino)-pent-3E-enol |
| 67 | 3-methyl-2-nitro-aniline | (2S)-amino-5-(2-nitro-3-methyl-phenylamino)-pent-3E-enol |

EXAMPLES 68–73

Following the procedure of Example 3, replacing the 3-fluoro-4-nitrotoluene with the reagent shown below, the products of Examples 68–73 are prepared as shown in Table 7.

TABLE 7

| Example number | Reagent | Product |
|---|---|---|
| 68 | 2,4-difluoronitrobenzene | (2S)-amino-5-(2-nitro-5-fluoro-phenylamino)-pent-3E-enol |
| 69 | 2,3-dichloronitrobenzene | (2S)-amino-5-(2-nitro-6-chloro-phenylamino)-pent-3E-enol |
| 70 | 2,4-dichloronitrobenzene | (2S)-amino-5-(2-nitro-5-chloro-phenylamino)-pent-3E-enol |
| 71 | 1,2,3-trichloronitrobenzene | (2S)-amino-5-(6-nitro-2,3-dichlorophenylamino)-pent-3E-enol |
| 72 | 3-fluoronitrophenol | (2S)-amino-5-(2-nitro-5-hydroxy-phenylamino)-pent-3E-enol |
| 73 | 2,6-dichloro-3-nitrotoluene | (2S)-amino-5-(2-nitro-5-chloro-6-methylphenylamino)-pent-3E-enol |

TABLE 7-continued

| Example number | Reagent | Product |
|---|---|---|
| | nitrotoluene | methylphenylamino)-pent-3E-enol |

EXAMPLES 74 AND 75 OF METHOD B (2S)-2-amino-5-(6-phenyl-2-nitrophenylamino)pentanoic acid Fluorination Method B Step 1. 2-acetamidobiphenyl To a solution of 10 mmol of 2-aminobiphenyl (K&K) in 1 L of 0.05M sodium acetate/acetic acid buffer (pH 5.0) is added 12 mmol of acetic anhydride, and the reaction is stirred at room temperature until complete (TLC). The solvent is removed in vacuo, and the title product is purified by chromatography.

Fluorination Method B Step 2. 2-acetamido-3-nitrobiphenyl

To a well stirred solution of 0.185 mol of 2-acetamidobiphenyl (from step 1) is added 50 mL of conc. $H_2SO_4$. The solution is cooled to 0° C. in an ice bath and stirred, and a mixture of 15.5 g of nitric acid and 12.5 g of sulfuric acid are added at such a rate that the temperature does not rise above 10° C. The reaction is stirred for 1 hour, then poured onto 250 g of crushed ice. The product is extracted from the mixture with dichloromethane. The extract is concentrated in vacuo, and the title product is purified by chromatography.

Fluorination Method B Step 3. 2-amino-3-nitrobiphenyl

The compound from step 2 is refluxed with 15 mL of 75% sulfuric acid for one hour, and the reaction is cooled, made basic with saturated sodium bicarbonate solution, and extracted with dichloromethane. The extract is concentrated, and the title product is purified by chromatography.

Fluorination Method B Step 4. 2-Fluoro-3-nitrobiphenyl

To a well stirred slurry of 2.2 mmol of nitrosonium tetrafluoroborate (Aldrich Chemical Co.) in 2.2 mL of dichloromethane cooled to 0° C. is added 2.0 mmol of the compound from step 3, at a rate sufficient to maintain the temperature below 5° C.

The reaction is stirred for 30 minutes, 15 mL of o-dichlorobenzene are added, and the dichloromethane is distilled off. The solution is then heated at 100°–155° C. until the reaction is complete, and the solvent is removed in vacuo to yield the title product.

Following the procedures of Fluorination Method B Steps 4 and 5, substituting the starting material shown below for the 2-amino-3-nitrobiphenyl of Fluorination Method B Step 3, the corresponding fluoro compound is prepared, which is reacted with N$^\alpha$BOC-L-ornithine according to the procedure of Example 2 in order to prepare the products of Examples 74 and 75, as shown in Table 8.

TABLE 8

| Example number | Starting Material | Product |
|---|---|---|
| 74 | 1-amino-5-bromo-2-nitronaphthalene | (2S)-amino-5-(2-nitro-5-bromo-naphthylamino)pentanoic acid |
| 75 | 1-amino-5-cyano-2-nitronaphthalene | (2S)-amino-5-(2-nitro-5-cyano-naphthylamino)pentanoic acid |

What is claimed is:
1. A compound of the formula:

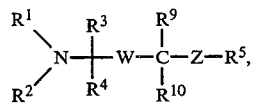

or a pharmaceutically-acceptable salt, ester, amide or prodrug thereof, wherein
$R^1$ is selected from the group consisting of
(1) hydrogen;
(2) $C_1$-$C_6$-alkyl;
(3) $C_6$-$C_{12}$-aryl-$C_1$-$C_4$-alkyl,;
(4) substituted $C_6$-$C_{12}$-aryl-$C_1$-$C_4$-alkyl;
(5) N-protecting group;
(6) —CO—$C_1$-$C_6$-alkyl;
(7) —CO—$C_6$-$C_{12}$-aryl;
(8) —CO-substituted $C_6$-$C_{12}$-aryl;
(9) —CO—$C_6$-$C_{12}$-aryl-$C_1$-$C_4$-alkyl;
(10) —CO-substituted $C_6$-$C_{12}$-aryl-$C_1$-$C_4$-alkyl; and
(11) —CO—Het;
$R^2$ is hydrogen when $R^1$ is selected from options (5)–(11) above, or when $R^1$ is selected from options (1)–(4) above, hydrogen, $C_1$-$C_6$-alkyl, $C_6$-aryl-$C_1$-$C_4$-alkyl, or substituted $C_6$-aryl-$C_1$-$C_4$-alkyl;
$R^3$ is selected from the group consisting of:
(1) —CO—$OR^6$, wherein $R^6$ is hydrogen, $C_1$-$C_6$-alkyl, $C_2$-$C_6$-alkenyl, cyclo-$C_3$-$C_7$-alkyl, $C_6$-$C_{12}$-aryl, substituted $C_6$-$C_{12}$-aryl, $C_6$-$C_{12}$-aryl-$C_1$-$C_4$-alkyl, or substituted $C_6$-$C_{12}$-aryl-$C_1$-$C_4$-alkyl;
(2) —$CHR^7$—$OR^8$, wherein $R^7$ is hydrogen, $C_1$-$C_6$-alkyl, cyclo-$C_3$-$C_7$-alkyl, $C_2$-$C_4$-alkenyl, or $C_6$-$C_{12}$-aryl: and $R^8$ is hydrogen, $C_1$-$C_6$-alkyl, or an oxygen protecting group; and

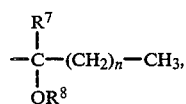

wherein n is 0–2, and $R^7$ and $R^8$ are as defined above;
$R^4$ is hydrogen, $C_1$-$C_6$-alkyl, $C_6$-$C_{12}$-aryl-$C_1$-$C_3$-alkyl, or substituted $C_6$-$C_{12}$-aryl-$C_1$-$C_3$-alkyl;
W is selected from
(a) $C_2$-$C_4$-alkylene;
(b) $C_2$-$C_4$-alkenylene;
(c) $C_2$-$C_4$-alkynylene;
(d) 1,4-($C_5$-$C_7$-cycloalkylene);
(e) 1,4-($C_5$-$C_7$-cycloalkenylene);
(f) phenylene;
(g) $C_1$-$C_3$-alkylene-phenylene; and
(h) phenylene-$C_1$-$C_3$-alkylene; and $R^9$ and $R^{10}$ are independently hydrogen or $C_1$-$C_6$-alkyl;
Z is S or $NR^{11}$, wherein $R^{11}$ is hydrogen, $C_1$-$C_6$-alkyl, $C_6$-$C_{12}$-aryl-$C_1$-$C_4$-alkyl or substituted $C_6$-$C_{12}$-aryl-$C_1$-$C_4$-alkyl; and
$R^5$ is

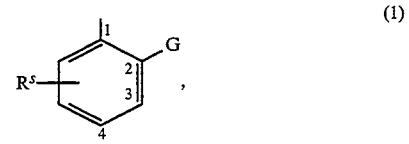

wherein G is either nitro or cyano; and
$R^S$, which may be substituted at one or two or positions 3-, 5- or 6-, represents one or two substituents independently selected from the group consisting of:
(a) halogen;
(b) $C_1$-$C_4$-alkyl;
(c) $C_1$-$C_4$-alkoxy;
(d) $C_1$-$C_4$-thioalkoxy;
(e) hydroxy;
(f) carbo-$C_1$-$C_4$-alkoxy;
(g) cyano; and
(h) halo-$C_1$-$C_4$-alkyl; or

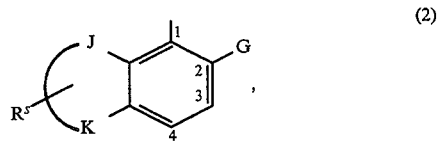

wherein G and $R^S$ are as defined above, and J and K taken together with the existing ring represent a fused bi- or tricyclic carbocycle of from 9–14 carbon atoms, wherein $R^S$ may be substituted anywhere within the entire bi- or tricyclic ring system except the 4-position.
2. A compound according to claim 1, wherein $R^1$ is hydrogen or an N-protecting group, $R^2$ is hydrogen, $R^4$ is hydrogen, $R^5$ is selected from option (1), wherein G is $NO_2$ and $R^S$ is one substituent as defined in claim 1 and is substituted at the 5-position, and $R^3$, $R^9$, $R^{10}$ and Z are as defined in claim 1.
3. A compound according to claim 1, which is:
(2S)-2-Amino-5-(5-methyl-2-nitrophenylamino)pentanoic acid;
(2S)-2-Amino-5-(5-methyl-2-nitrophenylamino)-pent-3E-en-1-ol;
2-Amino-5-(5-methyl-2-nitrophenylamino)-1-pentanol;
(2S)-2-Amino-5-(5-hydroxy-2-nitrophenylamino)pentanoic acid;
(2S)-2-Amino-5-(5-methoxy-2-nitrophenylamino)pentanoic acid;
(2S)-2-Amino-5-(2-chloro-6-nitrophenylamino)pentanoic acid;
(2S)-2-Amino-6-(2-nitro-5-methylphenylamino)hexanoic acid;
(2S)-2-Amino-5-(5-methyl-2-nitrophenylthioxy)pentanoic acid;
(2R)-2-(N-(1,1-Dimethylethoxycarbonyl)amino)-5-(5-methyl-2-nitrophenylamino)pentanoic acid;
(2R)-2-Amino-5-(5-methyl-2-nitrophenylamino)pentanoic acid;

2-Amino-4-(5-methyl-2-nitrophenylamino)butanoic acid;
(2S)-2-Amino-6-(2-nitrophenyamino)hexanoic acid;
(2S)-2-(Benzyloxycarbonylamino)-5-(5-methyl-2-nitrophenoxy)pentanoic acid t-butyl ester;
(2S)-3-[2-(2-Nitro-5-methylphenylamino)ethylthioxy]-propanoic acid;
$N^2$-Boc-2-amino-5-(5-methyl-2-nitrophenylamino)-1-phenyl-1-pentanol;
$N^3$-Boc-3-amino-6-(5-methyl-2-nitrophenylamino)-2-phenyl-2-hexanol;
2(S)-Amino-5-(5-methyl-2-nitrophenylthioxy)pentanol;
$N^2$-Hexanoyl-(2S)-2-amino-5-(5-methyl-2-nitrophenylamino)pentanoic acid;
$N^2$-Hexanoyl-(2S)-2-amino-5-(5-methyl-2-nitrophenylthioxy)pentanoic acid;
2-Amino-5-(5-methyl-2-nitrophenylamino)-1-phenyl-1-pentanol;
3-Amino-6-(5-methyl-2-nitrophenylamino)-2-phenyl-2-hexanol;
4-(5-Methyl-2-nitrophenylamino)phenyl-(S)-glycine;
$N^2$-Benzoyl-2(S)-amino-5-(5-methyl-2-nitrophenylamino)pentanoic acid;
$N^2$-Acetyl-2(S)-amino-5-(5-methyl-2-nitrophenylamino)pentanoic acid;
$N^2$-Phenylacetyl-2(S)-amino-5-(5-methyl-2-nitrophenylamino)pentanoic acid;
$N^2$-Trifluoroacetyl-2(S)-amino-5-(5-methyl-2-nitrophenylamino)pentanoic acid;
$N^2$-(4-Phenyl-2E-butenoyl)-2(S)-amino-5-(5-methyl-2-nitrophenylamino)pentanoic acid;
$N^2$-(2E-Butenoyl)-2(S)-amino-5-(5-methyl-2-nitrophenylamino)pentanoic acid;
$N^2$-(2-Methylpropanoyl)-2 (S)-amino-5-(5-methyl-2-nitrophenylamino)pentanoic acid;
$N^2$-(2-Furoyl)-2(S)-amino-5-(5-methyl-2-nitrophenylamino)pentanoic acid;
$N^2$-(Cyclohexanecarbonyl)-2(S)-amino-5-(5-( methyl-2-nitrophenylamino)pentanoic acid;
$N^2$-(Thiopheneacetyl)-2(S)-amino-5-(5-methyl-2-nitrophenylamino)pentanoic acid;
$N^2$-(Cyclopropanecarbonyl)-2 (S)-amino-5-(5-(methyl-2-nitrophenylamino)pentanoic acid;
$N^2$-Benzoyl-2(S)-amino-5-(5-methyl-2-nitrophenylthioxy)pentanoic acid;
$N^2$-Acetyl-2(S)-amino-5-(5-methyl-2-nitrophenylthioxy)pentanoic acid;
$N^2$-Phenylacetyl-2(S )-amino-5-(5-methyl-2-nitrophenylthioxy)pentanoic acid;
$N^2$-Trifluoroacetyl-2(S)-amino-5-(5-methyl-2-nitrophenylthioxy)pentanoic acid;
$N^2$-(4-Phenyl-2E-butenoyl)-2(S)-2-amino-5-(5-methyl-2-nitrophenylthioxy)pentanoic acid;
$N^2$-(2E-Butenoyl)-2(S)-amino-5-(5-methyl-2-nitrophenylthioxy)pentanoic acid;
$N^2$-(2-Methylpropanoyl)-2(S )-amino-5-(5-methyl-2-nitrophenylthioxy)pentanoic acid;
$N^2$-(2-Furoyl)-2(S)-amino-5-(5-methyl-2-nitrophenylthioxy)pentanoic acid;
$N^2$-(Cyclohexanecarbonyl)-2(S)-amino-5-(5-methyl-2-nitrophenylthioxy)pentanoic acid;
$N^2$-(Thiopheneacetyl)-2(S)-amino-5-(5-methyl-2-nitrophenylthioxy)pentanoic acid;
$N^2$-(Cyclopropanecarbonyl)-2(S)-amino-5-(5-methyl-2-nitrophenylthioxy)pentanoic acid;
3-Amino-6-(5-methyl-2-nitrophenylamino)-2-hexanol;
4-Amino-7-(5-methyl-2-nitrophenylamino)-1-hepten-3-ol;
4-Amino-7-(5-methyl-2-nitrophenylamino)-3-heptanol;
5-Amino-8-(5-methyl-2-nitrophenylamino)-2-methyl-4-octanol;
5-Amino-8-(5-methyl-2-nitrophenylamino)-1-octen-4-ol;
6-Amino-9-(5-methyl-2-nitrophenylamino)-5-nonanol;
2-Amino-5-(5-methyl-2-nitrophenylamino)-1-phenyl-1-pentanol;
2-Amino-5-(5-methyl-2-nitrophenylamino)-1-(2'-thienyl)-1-pentanol;
2-Amino-5-(5-methyl-2-nitrophenylamino)-1-(cyclopentyl)-1-pentanol;
2-Amino-5-(5-methyl-2-nitrophenylamino)-1-(cyclohexyl)-1-pentanol;
(2S)-Amino-5-(2-nitro-5-bromonaphthylamino)-pent-3E-enol;
(2S)-Amino-5-(6-nitro-2,3-dimethyl-phenylamino)-pent-3E-enol;
(2S)-Amino-5-(2-nitro-5-chloro-phenylamino)-pent-3E-enol;
(2S)-Amino-5-(2-nitro-6-methyl-phenylamino)-pent-3E-enol;
(2S)-Amino-5-(2-nitro-3-methyl-phenylamino)-pent-3E-enol;
(2S)-Amino-5-(2-nitro-5-fluoro-phenylamino)-pent-3E-enol;
(2S)-Amino-5-(2-nitro-6-chloro-phenylamino)-pent-3E-enol;
(2S)-Amino-5-(2-nitro-5-chloro-phenylamino)-pent-3E-enol;
(2S)-Amino-5-(6-nitro-2,3-dichloro-phenylamino)-pent-3E-enol;
(2S)-Amino-5-(2-nitro-5-hydroxy-phenylamino)-pent-3E-enol;
(2S)-Amino-5-(2-nitro-5-chloro-6-methylphenylamino)-pent-3E-enol;
(2S)-Amino-5-(2-nitro-5-fluoro-phenylamino)-pent-3E-enol;
(2S)-Amino-5-(2-nitro-6-chloro-phenylamino)-pent-3E-enol;
(2S)-Amino-5-(2-nitro-5-chloro-phenylamino)-pent-3E-enol;
(2S)-Amino-5-(6-nitro-2,3-dichloro-phenylamino)-pent-3E-enol;
(2S)-Amino-5-(2-nitro-5-hydroxy-phenylamino)-pent-3E-enol;
(2S)-Amino-5-(2-nitro-5-chloro-6-methylphenylamino)-pent-3E-enol;
(2S)-Amino-5-(2-nitro-5-bromo-naphthylamino)pentanoic acid; or
(2S)-Amino-5-(2-nitro-5-cyano-naphthylamino)pentanoic acid.

4. A compound according to claim 3, which is (2S)-2-Amino-5-(5-methyl-2-nitrophenylamino)pentanoic acid;
2-Amino-5-(5-methyl-2-nitrophenylamino)-pent-3E-en-1-ol;
2-Amino-5-(5-methyl-2-nitrophenylamino)-1-pentanol;
(2S)-2-Amino-5-(5-methyl-2-nitrophenylthioxy)pentanoic acid;
$N^2$-Boc-2-amino-5-(5-methyl-2-nitrophenylamino)-1-phenyl-1-pentanol; or
$N^3$-Boc-3-amino-6-(5-methyl-2-nitrophenylamino)-2-phenyl-2-hexanol.

5. A pharmaceutical composition for treating disorders of the vascular system or diseases of the cartilage characterized by the regulation of soluble guanylate cyclase or nitric oxide synthase activity, comprising a pharmaceutically-acceptable carrier and a therapeutically-effective amount of a compound according to claim 1.

6. A method for selectively-regulating soluble guanylate cyclase or nitric oxide synthase activity comprising administering to a patient in need of such treatment a therapeutically-effective amount of a compound according to claim 1.

7. A method for treating hypotension, hypertension, coronary vasospasm, cerebral vasoconstriction, cardiomyopathy, atherogenesis, atherosclerosis, myocardial ischemia, cerebral ischemia, diabetes, endotoxemia, sepsis, asthma, rhinitis, synovitis, chondroarthritis or osteoarthritis, comprising administering to a patient in need of such treatment a therapeutically-effective amount of a compound according to claim 1.

8. A method for treating disorders of the vascular system or diseases of the cartilage characterized by the regulation of soluble guanylate cyclase or nitric oxide synthase activity, comprising administering a pharmaceutically-acceptable carrier containing a therapeutically-effective amount of 2-amino-5-(2-nitrophenoxy)-valeric acid.

* * * * *